US007015330B2

United States Patent
Nidam et al.

(10) Patent No.: US 7,015,330 B2
(45) Date of Patent: Mar. 21, 2006

(54) SULFONATION METHOD FOR ZONISAMIDE INTERMEDIATE IN ZONISAMIDE SYNTHESIS AND THEIR NOVEL CRYSTAL FORMS

(75) Inventors: Tamar Nidam, Yehud (IL); Marioara Mendelovici, Rechovot (IL); Eduard Schwartz, Rehovot (IL); Shlomit Wizel, Petah Tiqva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/288,135

(22) Filed: Nov. 5, 2002

(65) Prior Publication Data

US 2003/0144527 A1 Jul. 31, 2003

Related U.S. Application Data

(63) Continuation-in-part of application No. 10/233,190, filed on Aug. 29, 2002.

(60) Provisional application No. 60/316,109, filed on Aug. 30, 2001, provisional application No. 60/344,439, filed on Oct. 24, 2001.

(51) Int. Cl.
*C07D 261/20* (2006.01)
(52) U.S. Cl. ...................................................... 548/241
(58) Field of Classification Search ................. 548/241
See application file for complete search history.

(56) References Cited

U.S. PATENT DOCUMENTS

| 4,172,896 A | 10/1979 | Uno et al. |
| 2002/0183525 A1 * | 12/2002 | Mendelovici et al. ....... 548/241 |

FOREIGN PATENT DOCUMENTS

FR 2 428 033 * 1/1980

* cited by examiner

*Primary Examiner*—Taofiq Solola
*Assistant Examiner*—Rebecca Anderson
(74) *Attorney, Agent, or Firm*—Kenyon & Kenyon

(57) ABSTRACT

The present invention relates to a novel sulfonation of an intermediate of zonisamide. The sulfonation processes using chlorosulfonic acid as well as acetic anhydride and sulfuric acid in an organic solvent are disclosed. Crystalline forms of benzisoxazole methane sulfonic acid (BOS—H) and its salts (BOS—Na, BOS—Ca, and BOS—Ba) and their novel preparation processes are disclosed.

6 Claims, 23 Drawing Sheets

SULFONATION METHOD FOR ZONISAMIDE INTERMEDIATE IN ZONISAMIDE SYNTHESIS AND THEIR NOVEL CRYSTAL FORMS

CROSS-REFERENCE TO RELATED APPLICATIONS

This application is a Continuation-In-Part (CIP) of the U.S. Conventional application Ser. No. 10/233,190, filed on Aug. 29, 2002, which claims the benefits under 35 U.S.C. §1.119(e) of Provisional Application Ser. No. 60/316,109 filed Aug. 30, 2001 and Ser. No. 60/344,439 filed Oct. 24, 2001, the disclosure of which is incorporated by reference in its entirety herein.

FIELD OF THE INVENTION

The field of the invention is the sulfonation of a zonisamide intermediate and crystalline forms of the zonisamide intermediate in the form of acid and metallic salts. Within that field, the present invention relates most particular to novel sulfonation processes for preparing the zonisamide intermediate of benzisoxazole acetic acid and the crystalline forms thereof.

BACKGROUND OF THE INVENTION

Zonisamide is known as 1,2-benzisoxazole-3-methane sulfonamide or 3-(sulfamoylmethyl)-1,2-benzisoxazole. It has the following chemical formula:

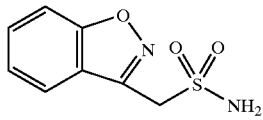

Zonisamide is currently available as an anti-epileptic agent which possesses anti-convulsant and anti-neurotoxic effects.

Several routes for zonisamide synthesis have been described in the literature. Two of these synthesis routes start from 4-hydroxy-coumarin via benzisoxazole acetic acid (hereinafter; BOA) and sodium salt of benzisoxazole methane sulfonic acid (hereinafter; BOS—Na).

Scheme 1 represents the first route for zonisamide synthesis. In this route, the zonisamide intermediate (BOA) is brominated followed by substitution of the bromine by sodium sulfite to give the advanced intermediate sodium salt of BOS (BOS—Na) as shown as follows:

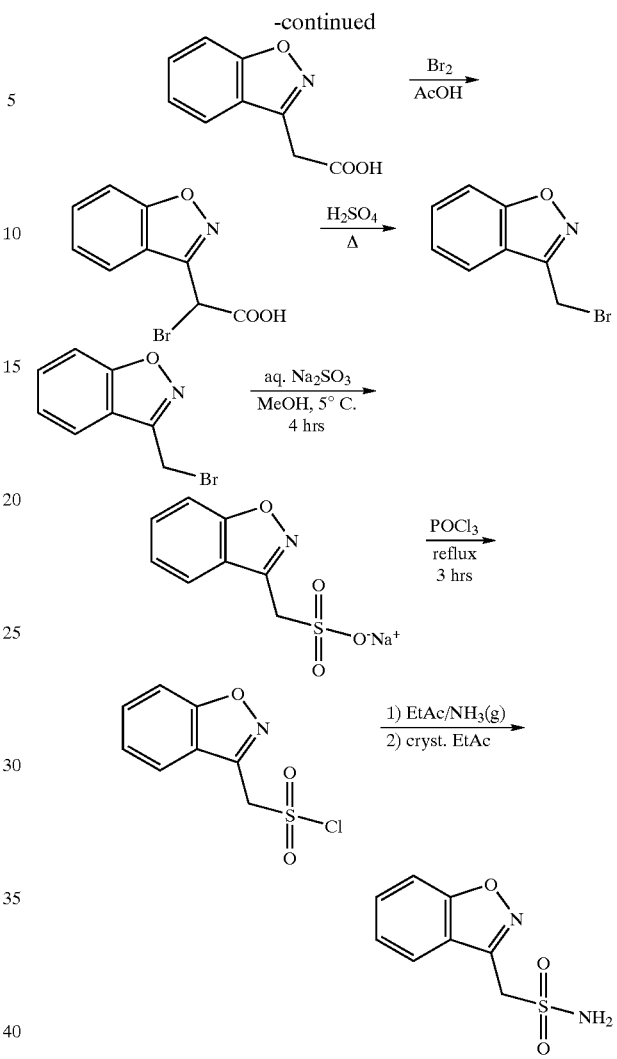

The synthetic method of the route shown in scheme 1 is a difficult method due to the great sensitivity of the reaction product.

The second method described in literature for zonisamide preparation includes the preparation of BOA starting from 4-hydroxy-coumarin, followed by the sulfonation reaction of BOA to BOS. The sulfonation reaction of the zonisamide intermediate (i.e., BOA) may be carried out with chlorosulfonic acid. The reagent chlorosulfonic acid is used in a large excess and it is also the reaction solvent. The sulfonation reaction with chlorosulfonic acid gives the disulfonated-benzisoxazole-derivative (S—BOS) as the main reaction by-product. The reactions of this synthetic method are shown in scheme 2:

Scheme 1

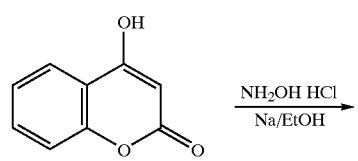

Scheme 2

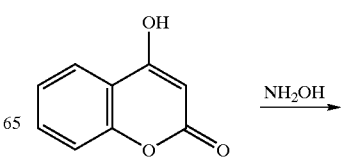

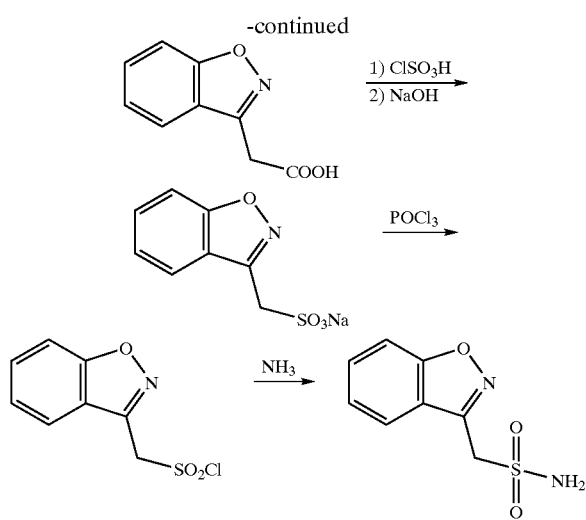

When the reaction is conducted in chlorosulfonic acid, the sulfonation is not selective. Disulfonated-benzisoxazole derivateive (S—BOS) is a main product of the reaction.

The synthetic pathway via the sulfonation reaction of BOA comprises two steps lesser as compared to the synthetic pathway via the bromination reaction. However, the sulfonation reaction requires a large amount of chlorosulfonic acid which poses undesirable environmental problems.

U.S. Pat. No. 4,172,896 by Uno H. et al. (assigned to Dainippon Pharmaceutical Co.) describes the preparation of zonisamide using the sulfonating agent chlorosulfonic acid: dioxane complex. A similar reagent ($SO_3$: dioxane complex) is known in the literature and was successfully used for the selective sulfonation of the aromatic ketones. Chlorosulfonic acid:dioxane is a selective sulfonating reagent and the disulfonated side products is obtained in a low quantity. The reaction is shown in scheme 3.

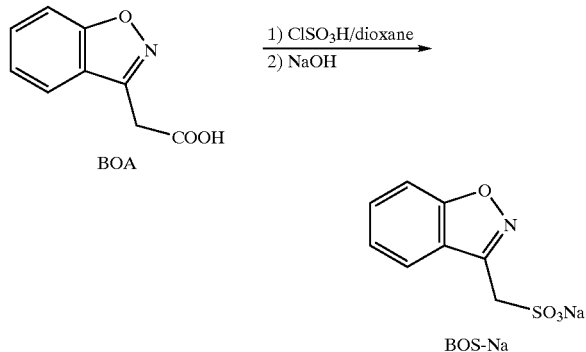

Although the sulfonation method using chlorosulfonic acid: dioxane complex is selective, this method is not safe because of the serious environmental problem of the dioxane present in the reaction waste.

There is a continuous need to improve the sulfonation method that is both convenient and environmentally safe. The present invention provides an unexpected novel sulfonation process to prepare the intermediate of zonisamide.

Neither patents have characterized the existence of any crystalline forms of this product. There is a continuing need to investigate crystalline forms of BOS which can provide useful intermediates for zonisamide synthesis.

We found that the product of the sulfonation reaction (BOS) may be isolated as sulfonic acid type compound (BOS—H) or as its salt (metallic salts). Not depending on the product type form, the reaction mixture is usually treated with water allowing the isolation of the product with variable water content. These compounds have the tendency to give hydrates.

Furthermore, it is generally known that alkyl- and aryl-sulfonic acids and their salts can exist as hydrated form (C. M. Suter in "The Organic Chemistry of Sulfur", J. Wiley, N.Y., 1946). The widely-known reagent p-toluene-sulfonic acid can exist as monohydrate. It is necessary to develop another method for preparation of the sodium salt of BOS.

SUMMARY OF THE INVENTION

According to one aspect, the present invention provides a sulfonation process for preparing benzisoxazole methane sulfonic acid (BOS).

Preferably, anhydride and sulfuric acid are employed in preparing benzisoxazole methane sulfonic acid (BOS) in a sulfonation process.

According to another aspect, the present invention provides a sulfonation process for preparing benzisoxazole methane sulfonic acid (BOS) employing chlorosulfonic acid in an organic solvent.

According to another aspect, the present invention provides a process for preparing an intermediate of zonisamide, comprising the steps of:
 a) preparing a mixture of chlorosulfonic acid and an organic solvent;
 b) adding benzisoxazole acetic acid to the mixture;
 c) heating the mixture; and
 d) isolating the intermediate of zonisamide.

According to another aspect, the present invention provides a sulfonation process for preparing benzisoxazole methane sulfonic acid (BOS) employing acyl-sulfates or in situ prepared acyl-sulfates. In situ prepared acyl-sulfates may be obtained from anhydrides and sulfuric acid ($H_2SO_4$), acyl-halides and $H_2SO_4$, or carboxylic acids and $H_2SO_4$.

Most preferably, acetic anhydride and sulfuric acid are employed in preparing benzisoxazole methane sulfonic acid in a sulfonation process.

According to another aspect, the present invention provides a process for preparing an intermediate of zonisamide, comprising the steps of:
 a) preparing an acyl sulfate in a solution;
 b) adding benzisoxazole acetic acid to the solution wherein the benzisoxazole acid is sulfonated by the acyl sulfate to form the intermediate of zonisamide;
 c) heating the solution; and
 d) isolating the intermediate of zonisamide.

According to another aspect, the present invention provides a process for preparing an intermediate of zonisamide, comprising the steps of:
 a) preparing a mixture of benzisoxazole acetic acid and an anhydride in a solvent to form a mixture;
 b) preparing an acyl sulfate in the mixture wherein the benzisoxazole acid is sulfonated by the acyl sulfate to form the intermediate of zonisamide;
 c) heating the mixture; and
 d) isolating the intermediate of zonisamide.

According to another aspect, the present invention provides benzisoxazole methane sulfonic acid substantially free of disulfonated benzisoxazole derivatives.

According to another aspect, the present invention provides zonisamide substantially free of disulfonated benzisoxazole derivatives.

According to another aspect, the present invention provides zonisamide substantially free of impurities and without the use of dioxane.

The present invention generally relates to the crystalline forms of benzisoxazole methane sulfonic acid (BOS—H) and its salts.

The present invention provides the crystalline forms of BOS with a metal cation. Preferably, the present invention provides the crystalline forms of BOS—Na, BOS—Ca, and BOS—Ba. Other metallic salts include, but not limited to, potassium, magnesium, lithium, manganese, cobalt, iron, copper, nickel, zinc, silver and the like.

The present invention relates to the zonisamide intermediate BOS in the form of acid and metallic salts which are useful in the zonisamide synthesis.

The present invention provides the hydrated crystalline forms of BOS—H and its salts as intermediates in the zonisamide synthesis.

The present invention provides a novel crystal form of BOS—Na Form I, characterized by an X-Ray Powder Diffraction (XRD) having the most characteristic peaks at about 5.0, 17.3, 18.0, 18.6, and 19.7±0.2 degrees two theta.

The present invention provides a novel crystal form of BOS—Na Form I, characterized by an X-Ray Powder Diffraction (XRD) having the main peaks at about 5.0, 15.7, 16.5, 17.3, 18.6, 19.1, 19.7, 21.5, 22.8, 23.2, 23.5 and 24.3±0.2 degrees two theta.

The present invention provides a novel crystal form of BOS—Na Form I, characterized by a Furier Transform Infra Red Spectroscopy (FTIR) spectrum having the most characteristic peaks at about 3546, 3485, 3440, 1641, 669 and 593 cm$^{-1}$.

The present invention provides a novel crystal form of BOS—Na Form I, characterized by a Furier Transform Infra Red Spectroscopy (FTIR) spectrum having the following peaks at about 3546, 3485, 3440, 1612, 1513, 1439, 1410, 1382, 1234, 1199, 1048, 918, 855, 760, 669 and 593 cm$^{-1}$.

The present invention provides a novel crystal form of BOS—Na Form I having a water content of about 7%.

The present invention provides a novel crystal form of BOS—Na Form II, characterized by an X-Ray Powder Diffraction (XRD) having the main peaks at about 5.3, 16.6, 21.3 and 26.7±0.2 degrees two theta.

The present invention provides a novel crystal form of BOS—Na Form II, characterized by an X-Ray Powder Diffraction (XRD) having the most characteristic peaks at about 5.3, 15.9, 16.6, 21.3 and 26.7±0.2 degrees two theta.

The present invention provides a novel crystal form of BOS—Na Form II, characterized by a Furier Transform Infra Red Spectroscopy (FTIR) spectrum having the following peaks at about 3597, 3535, 3496, 3067, 2998, 2951, 1606, 1516, 1438, 1382, 1213, 1064, 1055, 743, 663, 588, 541 and 522 cm$^{-1}$.

The present invention provides a novel crystal form of BOS—Na Form II having a water content of about 1.8%.

The present invention provides a novel crystal form of BOS—Na Form III, characterized by an X-Ray Powder Diffraction (XRD) having the most characteristic peaks at about 5.0, 5.3, and 17.8±0.2 degrees two theta.

The present invention provides a novel crystal form of BOS—Na Form III, characterized by an X-Ray Powder Diffraction (XRD) having the main peaks at about 5.0, 5.3, 15.7, 17.8 and 21.4±0.2 degrees two theta.

The present invention provides a novel crystal form of BOS—Na Form III, characterized by a Furier Transform Infra Red Spectroscopy (FTIR) spectrum having the most characteristic peaks at about 3604, 1065, 812 and 696 cm$^{-1}$.

The present invention provides a novel crystal form of BOS—Na Form III, characterized by a Furier Transform Infra Red Spectroscopy (FTIR) spectrum having the following peaks at about 3604, 3495, 3067, 2998, 2951, 1605, 1516, 1438, 1382, 1215, 1136, 1065, 1052, 777, 747, 696, 588 and 521 cm$^{-1}$.

The present invention provides a novel crystal form of BOS—Na Form IV, characterized by an X-Ray Powder Diffraction (XRD) having the main peaks at about 4.5, 5.9, 8.8, 11.3, 16.3, 16.9, 19.0, 22.5, 23.9, 24.7, 25.0, 26.8, 28.1, 29.7, 30.9, 32.6, 33.6, 35.5, 36.6±0.2 degrees two theta.

The present invention provides a novel crystal form of BOS—Na Form IV, characterized by a Furier Transform Infra Red Spectroscopy (FTIR) spectrum having the following peaks at about 3431, 1567, 1416, 924, 862 and 586 cm$^{-1}$.

The present invention provides a novel crystal form of BOS—Na IV having a water content of about 2.9%.

The present invention provides a novel crystal form of BOS—Na Form V, characterized by an X-Ray Powder Diffraction (XRD) having the main peaks at about 6.7, 10.9, 16.1, 21.0, 21.2 and 22.2±0.2 degrees two theta.

The present invention provides a novel crystal form of BOS—Na Form V, characterized by a Furier Transform Infra Red Spectroscopy (FTIR) spectrum having the most characteristic peaks at about 3601, 3520, 1587, 1055, 793, and 753 cm$^{-1}$.

The present invention provides a novel crystal form of BOS—Ba Form V having a water content of less than about 1.5%.

The present invention provides a novel crystal form of BOS—Ba Form I, characterized by the following X-Ray Diffraction main peaks at about 5.2, 10.4, 12.0, 13.8, 15.6, 17.0, 23.9 and 25.4±0.2 degrees two theta.

The present invention provides a novel crystal form of BOS—Ba monohydrate, characterized by a Furier Transform Infra Red Spectroscopy (FTIR) spectrum having the following peaks at about 3544, 3491, 2985, 2943, 1626, 1610, 1509, 1437, 1383, 1369, 1223, 1209, 1175, 1153, 1055, 1043, 911, 869, 752, 651, 603, 543 and 511 cm$^{-1}$.

The present invention provides a novel crystal form of BOS—Ba monohydrate having a water content about 3.5%.

The present invention provides a novel crystal form of BOS—Ca Form I, characterized by having the following X-Ray Diffraction main peaks at about 5.4, 11.7, 16.0, 16.7, 17.7, 18.1, 19.1, 20.8, 24.5, 24.9 and 29.2±0.2 degrees two theta.

The present invention provides a novel BOS—H monohydrate Form I, characterized by having the following X-Ray Diffraction main peaks at about 13.8, 14.4, 17.4, 17.8, 21.8, 22.2, 25.8, 27.8±0.2 degrees two theta.

The present invention provides a novel BOS—H monohydrate Form I having a water content about 7.6%.

The present invention provides a novel process for preparing a BOS—Na Form I. The present invention further provides a process of preparing a BOS—Na Form I, comprising the steps of: 1) preparing a mixture of chlorosulfonic acid in an organic solvent; 2) adding BOA to the mixture; 3) treating the mixture with NaOH to raise pH; and 4) isolating the BOS—Na Form I.

The present invention provides a novel process for preparing a BOS—Na Form I. The present invention further provides a process of preparing a BOS—Na Form I, comprising the steps of: 1) preparing a mixture of an anhydride and sulfuric acid to form acyl-sulfate in the presence of an organic solvent; 2) adding BOA to the mixture; 3) treating the mixture with NaOH to raise pH; 4) cooling the mixture to form a precipitate; 5) drying the precipitate; and 6) keeping the dry precipitate at room temperature to obtain the BOS—Na Form I.

The present invention provides a novel process for preparing a BOS—Na Form II. The invention further provides a process of preparing a BOS—Na Form II, comprising the steps of: 1) preparing a mixture of an anhydride and sulfuric acid to form acyl-sulfate in the presence of ethyl acetate; 2) adding BOA to the mixture; and 3) treating the mixture with NaOH to raise pH; 4) cooling the mixture to form a precipiate; and 5) drying the preciptate at 80° C. to obtain the BOS—Na Form II.

The present invention provides a novel process for preparing BOS—Na Form III. The present invention further provides a method of preparing a BOS—Na Form III, comprising the steps of: 1) preparing a mixture of an anhydride and sulfuric acid to form acyl-sulfate in the presence of toluene; 2) adding BOA to the mixture; 3) treating the mixture with NaOH to raise pH; 4) cooling the mixture to form a precipitate; and 5) drying the preciptate at 80° C. to obtain the BOS—Na Form III.

The present invention provides a novel process for preparing BOS—Na Form IV. The present invention further provides a method of preparing a BOS—Na Form IV, comprising the steps of: 1) preparing a slurry of BOS—Na in the presence of ethanol; 2) heating the slurry to form a gel; and 3) evaporating the ethanol to obtain the BOS—Na Form IV. Preferably, the slurry is heated until it reaches a gel-like stage. Preferably, the slurry is heated at a reflux temperature of ethanol. Preferably, slurry of BOS—Na may be prepared in the presence of other lower alkyl alcohol including isopropanolol or methanol. Preferably, ethanol is 75% to 100%. Most preferably, the ethanol is an absolute ethanol (100%).

The present invention provides a novel process for preparing a BOS—Na Form V. The present invention further provides a method of preparing a BOS—Na Form V, comprising the steps of: 1) preparing a mixture of an anhydride and sulfuric acid to form acyl-sulfate; 2) adding BOA to the mixture; 3) treating the mixture with NaOH to raise pH; 4) cooling the mixture to form a precipitate; and 5) drying the precipitate at about 85° C. to obtain the BOS—Na Form V.

The present invention provides a novel process for preparing BOS—Ba monohydrate. The present invention further provides a method of preparing a BOS—Ba monohydrate, comprising the steps of: 1) preparing a mixture of chlorosulfonic acid and an organic solvent; 2) adding BOA to the mixture; 3) treating the mixture with Ba(OH)$_2$, and 4) isolating the BOS—Ba monohydrate.

The present invention provides a novel process for preparing a BOS—Ca dihydrate. The present invention further provides a method of preparing a BOS—Ca dihydrate, comprising the steps of: 1) preparing a mixture of chlorosulfonic acid and an organic solvent; 2) adding BOA the mixture; 3) treating the mixture with Ca(OH)$_2$; and 4) isolating the BOS—Ca dihydrate.

The present invention provides a novel process for preparing a BOS—H monohydrate. The present invention further provides a process of preparing a BOS—H monohydrate, comprising the steps of: 1) preparing a mixture of chlorosulfonic acid in an organic solvent; 2) adding BOA to the mixture; 3) treating the mixture with NaOH to raise pH; and 4) isolating the BOS—H monohydrate.

BRIEF DESCRIPTION OF THE DIAGRAMS

DETAILED DESCRIPTION OF THE INVENTION

Figure 1:
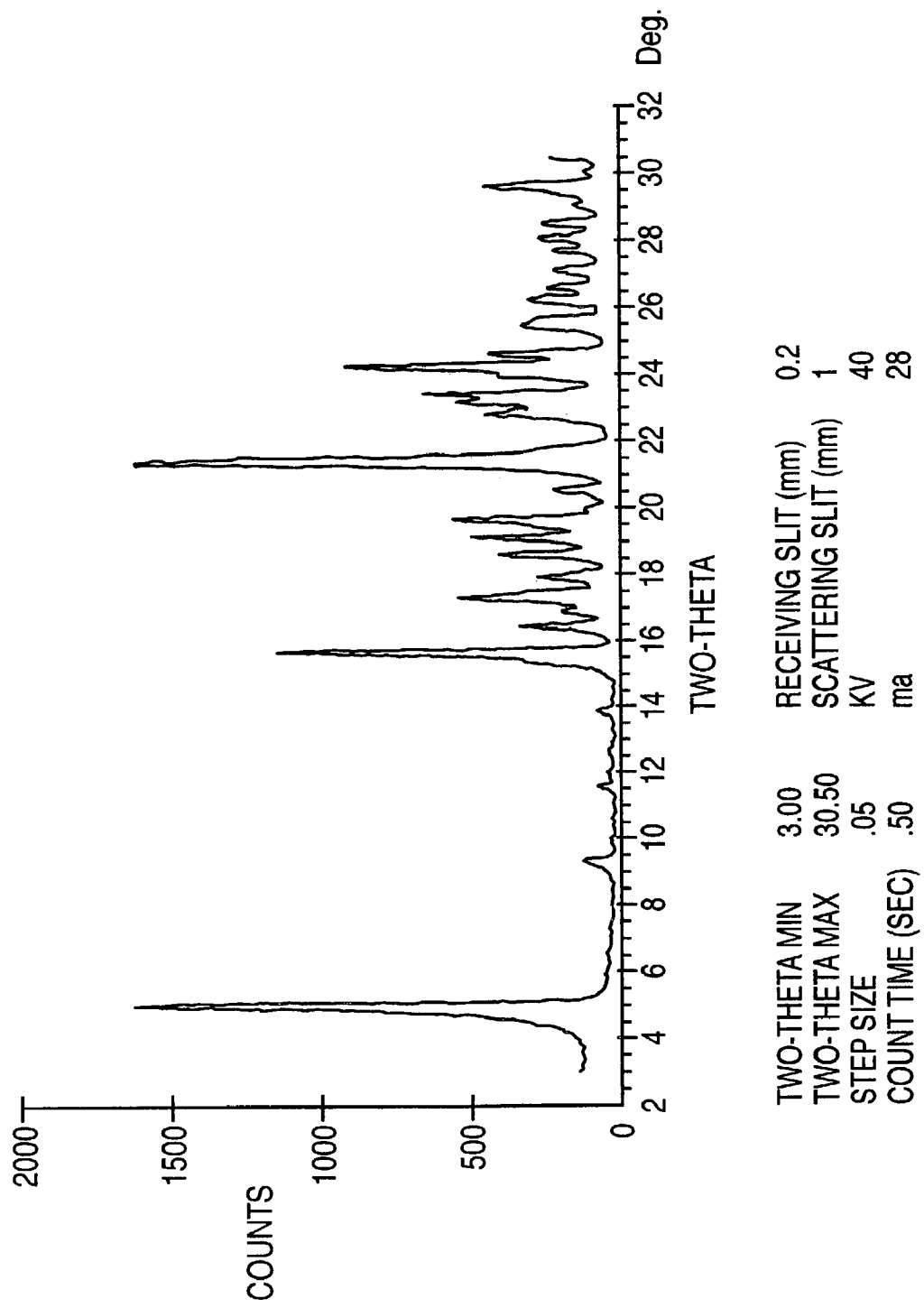
FIG. 1 depicts the X-ray Powder Diffraction (XRD) Pattern for BOS—Na monohydrate novel Form I.

As used throughout the text, the following abbreviations are used: benzisoxazole acetic acid (BOA); benzisoxazole-methane-sulfonic acid (BOS); sodium salt of benzisoxazole-methane-sulfonic acid (BOS—Na); calcium salt of benzisoxazole-methane-sulfonic acid (BOS—Ca); barium salt of benzisoxazole-methane-sulfonic acid (BOS—Ba); sulfuric acid ($H_2SO_4$), chlorosulfonic acid ($ClSO_3H$), disulfonated benzisoxazole-derivative (S-BOS) which is a disulfonation product; tertiary-butyl alcohol (t-BuOH).

As used herein, room temperature refers to ambient temperature. Unless otherwise stated, % refers to % by weight. The term "slurry" refers to a free-flowing pumpable suspension of a solid material in a liquid; and the term "gel-like" refers to a physical condition of a colloid system, whereby the colloid system bears a semblance of a solid, in which a solid is dispersed in a liquid.

As used herein, the term "TGA" refers to thermogravimetric analysis. The Karl Fisher assay for determining water content is well known and is described in *Pharmacopeial Form*, Vol. 24, No. 1, p. 5438 (January–February 1998). Such an assay permits the determination of water content of a crystal form based on the Loss on Drying Method. TGA is a measure of the thermally induced weight loss of a material as a function of the applied temperature.

As used herein, the term "FTIR" refers to Furier Transform Infra Red Spectroscopy. FTIR is a well-known spectroscopy analysis in which absorption of IR energy by the sample results from transitions between molecular vibrational energy levels. FTIR is used, in modem practice, mainly for identification of functional groups in the molecule. However, different polymorphic forms also show differences in FTIR. The FTIR spectra were collected using Diffuse Reflectance Technique; scanning range: 4000–400 cm$^{-1}$, 16 scans, resolution: 4.0 cm$^{-1}$.

The present invention relates to more convenient methods for sulfonation of benzisoxazole acetic acid (BOA). The sulfonation process involves a reaction that does not use dioxane and eliminates the problem of the waste.

The present sulfonation method relates to the sulfonation reaction of benzisoxazole acetic acid using chlorosulfonic acid in organic solvents like dichloroethane, dichloromethane, toluene, ethylene glycol-dimethylether or heptane using a slight excess of the sulfonating reagent. Under such conditions, the sulfonation reaction is selective.

The present sulfonation reaction solvent may be a polar solvent like ethyl-acetate, dichloroethane, t-BuOH, or a non-polar solvent like hexanes, heptane, cyclohexane, toluene, dichlorobenzene or mixture thereof.

The present invention has the advantage of the sulfonation reaction using chlorosulfonic acid wherein the reaction is selective and proceeds mainly in the alpha position of benzisoxazole acetic acid. The disulfonated product is obtained at a level of about 2–5%.

The present invention also provides a process for preparing benzisoxazole methane sulfonic acid (BOS) employing acyl-sulfates or in situ prepared acyl-sulfates. In situ prepared acyl-sulfates may be obtained from anhydrides and sulfuric acid, acyl-halides and sulfuric acid, or carboxylic acids and sulfuric acid; all organic acids including fatty acids may react in this way.

A more preferred sulfonation process involves the use of the acyl-sulfates obatined from anhydrides and H$_2$SO$_4$ or acyl-halide and H$_2$SO$_4$. Examples of acyl-sulfates of a practical interest include acetyl-sulfate (obtained from Ac$_2$O/H$_2$SO$_4$ or acetylchloride/H$_2$SO$_4$), propionyl-sulfate, butryl-sulfate or other acyl-sulfate (obtained in the same manner from the corresponding anhydride or acyl-halide and H$_2$SO$_4$) which are more economics and more easy to handle.

The more preferred method uses acetic anhydride and sulfuric acid (H$_2$SO$_4$). The more preferred sulfonating reagent "anhydride acetic/H$_2$SO$_4$" is economic, easy for handling, and excludes the use of dioxane.

The sulfonation process using acyl-sulfates is even more selective than that of chlorosulfonic acid in organic solvent. The selective sulfonation proceeds preferentially in the alpha position and a substantially pure zonisamde intermediate (e.g., sodium salt of BOS) is obtained. Particularly, the disulfonated side-product present in the substantially pure zonismade intermediate is at a low level up to 1%.

The sulfonation process for the Ac$_2$O/H$_2$SO$_4$ involves a reaction that is performed in polar and non-polar solvents. The polar solvents include ethylacetate, ethylcellosolve, methylcellosolve, dichloroethane, dichloromethane, chloroform or mixture thereof and the like. The non-polar solvents include toluene, heptane, hexanes, alkanes or mixtures thereof and the like.

We observed that the product of the sulfonation reaction in the zonisamide process may be obtained with a variable water content. This observation is valid for BOS—H and its salts also.

The present invention provides new crystal forms of BOS. The polymorphic modification of this zonisamide intermediate are chemically identical, but exhibit differences in their physical properties such as X-Ray Diffractrogram, Furier Transform Infra Red Spectroscopy and etc. Differences in mechanical behavior or in the dissolution properties of different polymorphic modifications can significantly influence the ease of processing or the bioavailability of these compounds. It is desirable to obtain various crystal or polymorphic forms of zonisamide intermediates.

We observed BOS is a hygroscopic compound. We further observed that BOS—H is a more hygroscopic compound than its alkaline or earth-alkaline salts. Practically, it is recommended to isolate the product as salt rather than the free sulfonic acid.

BOS—H and its salts are readily soluble in water and this makes difficult their separation from the reaction mixture.

However, the salts of sulfonic acid are less water-soluble than the inorganic salts and it is preferable to proceed to the conversion of sulfonic acid into its salt (sodium, calcium or barium salt) and to isolate them by salting out with an inorganic salt.

The salts of BOS having a practical interest include generally alkaline salts and earth-alkaline salts. Examples of BOS salts include sodium (Na), potassium (K), calcium (Ca), barium (Ba), and Magnesium (Mg). In general, BOS is a strong acid having approximately the same strength as H$_2$SO$_4$ and can forms salts with various cations including silver (Ag), cadium (Ca), zinc (Zn), mercury (Hg), aluminium (Al), and the like.

The present invention further provides a crystalline form of benzisoxazole methane sulfonic acid wherein the metal cation is selected from sodium, calcium, barium, potassium, magnesium, lithium, manganese, cobalt, iron, copper, nickel, zinc, silver, and the like.

BOS—H and its sodium (Na—), calcium (Ca—) or barium (Ba—) salts are usually obtained from the reaction with 1–2% water content but they can absorb water from the medium until the hydrate is obtained.

The present invention is described in details with reference to examples. The present invention is by no means restricted to these specific examples. The experiments of the invention are summarized in the following table.

Synthesis of the Zonisamide Intermediate (BOS)

SYNTHESIS OF THE ZONISAMIDE INTERMEDIATE (BOS)

| Experiments | Reagent, eq. nr/solvent | Reaction conditions: Temp., time | Sample type | Purity profile HPLC, % Area, BOS-Na | S-BOS | BOA |
|---|---|---|---|---|---|---|
| 1 | 1.3 eq. ClSO$_3$H/dichloro-ethane | Reflux, 1.5 hours | Reaction mixture | 90 | 5.4 | 0.4 |
|  |  |  | Isolated product | 99.8 | 0.15 |  |
| 2 | 1.3 eq. ClSO$_3$H/Ethylenglycol-dimethyl-ether | 50° C., 20 hours | Reaction mixture | 58 |  | 34 |
|  |  |  | Isolated product | n.a. | n.a. | n.a. |
| 3 | 1.3 eq. ClSO$_3$H/Heptane + dichloro-ethane | 65° C., 3 hours | Reaction mixture | 95 | 1.8 | 3.1 |
|  |  |  | Isolated product | 99.5 | 0.15 | 0.4 |
| 4 | 1.7 eq. ClSO$_3$H/Toluene | Reflux, 20 hours | Reaction mixture | 63.5 | 3 | 32 |
| 5 | 1.3 eq. Ac$_2$O/H$_2$SO$_4$/dichloro-ethane | 75° C., 2 hours | Reaction mixture | 85.5 | 0.8 | 0.1 |
| 6 | 2.7 eq. Ac$_2$O/H$_2$SO$_4$/Tol. | Reflux, 9 hours | Reaction mixture | 83.4 | n.d. | 10.7 |
|  |  |  | Isolated product | 92.4 | n.d. | 4.5 |
| 7 | 1.3 eq. Ac$_2$O/H$_2$SO$_4$/Heptane | 90° C., 1 hours | Isolated product | 98.4 | n.d. | 1.5 |
| 8 | 1.3 eq. Ac$_2$O/H$_2$SO$_4$/dichloro-benzene | ~100° C., 1.5 hour | Reaction mixture | 98.5 | 0.2 | 0.2 |
|  |  |  | Isolated product | 99.7 | n.d. | 0.2 |
| 9 | 1.3 eq. Ac$_2$O/H$_2$SO$_4$/EtOAc | ~90° C., 4 hours | Reaction mixture | 99.2 | 0.5 | n.d. |
|  |  |  | Isolated product | 100 |  |  |
| 10 | 1.3 eq. Ac$_2$O/H$_2$SO$_4$/EtOAc reverse addition of the reagents: H$_2$SO$_4$ added to the reaction mixture | ~90° C., 4 hours | Reaction mixture | 99.1 | 0.5 | n.d. |
|  |  |  | Isolated product | 100 |  |  | n.a. not analyzed
n.d. not detected

Experimental Procedures

EXAMPLE 1

Preparation of BOS—Na: Ac$_2$O/H$_2$SO$_4$ in ethyl-acetate

In a 250 mL reactor, equipped with thermometer, mechanical stirrer and condenser was charged ethyl acetate (80 mL), H$_2$SO$_4$, 98% (22 grams, 1.3 eq.) and acetic anhydride (23 grams, 1.3 eq.) and the mixture was cooled to −5° C.

To the above mixture, BOA was added (20 grams, 1 eq.). The reaction was then heated to reflux and the reflux was continued for 4 hours. After the reaction completion the reaction mixture was cooled to the room temperture and aqueous NaOH (10%) was added (120 mL). Upon stirring, the product precipitates as sodium salt. After 2 hours the product was filtrated, washed with ethyl acetate (2×25 mL) and dried in vacuum-oven at ~80° C. The yield was 20.33 grams BOS—Na having 100% purity by HPLC).

EXAMPLE 2

Preparation of BOS—Na: Ac$_2$O/H$_2$SO$_4$ in ethyl acetate by Drop-Wise Addition of H$_2$SO$_4$ In a 250 mL reactor, equipped with thermometer, mechanical stirrer and condenser was charged ethyl acetate (80 mL), acetic anhydride (23 grams, 1.3 eq.) and BOA (20 grams, 1 eq.). The mixture was cooled to about −5° C.

Maintaining the temperature below 0° C., H$_2$SO$_4$, 98% (22 grams, 1.3 eq.) was added drop-wise (the addition required about 20 min.). Then the reaction mixture was stirred at reflux for 4 hours. When the reaction was completed the mixture was cooled to room temperature and aqueous NaOH (10%) was added (120 mL). After 2 hours stirring at room temperature, the reaction product was filtrated, washed with ethyl acetate (2×25 mL) and dried in vacuum-oven ~80° C. The yield was 20.21 grams of BOS—Na that has a 100% purity by HPLC.

EXAMPLE 3

Preparation of BOS—Na: Ac$_2$O/H$_2$SO$_4$ in toluene

In a 100 mL three necked flask, equipped with thermometer, condenser and mechanical stirrer was charged toluene (40 mL), H$_2$SO$_4$, 98% (2 mL, 1.3 eq.) and acetic anhydride (3.5 mL, 1.3 eq.) at room temperature.

Then, benzisoxazole acetic acid (BOA) was added (5 grams) and the reaction mixture was heated to reflux. The reflux was continued for about 4.5 hours. To the chilled reaction mixture, more reagent was added (2 mL H$_2$SO$_4$, 98% and 3.5 mL acetic anhydride) and the heating was continued for additional 4 hours. After cooling of the reaction mixture to room temperature, ice was added and the mixture was stirred. The organic phase was discarded and to the aqueous phase solid NaOH was added (7.5 grams). The product precipitates upon cooling at ~5° C.; the solid was filtered, washed with toluene and dried in vacuum-oven at ~80° C. The yield was 7.6 g BOS—Na with 92.4% purity on HPLC.

EXAMPLE 4

Preparation of BOS—Na: ClSO$_3$H in dichloroethane

In a 100 mL three necked flask, equipped with thermometer, condenser and mechanical stirrer was charged dichloroethane (25 mL), 2.5 mL ClSO$_3$H (1.3 eq.), and BOA (5 grams). The reaction mixture was heated at reflux for 1.5 hours.

Water was added (30 mL) and the phases were separated. To the aqueous phase, solid NaOH was added (3.5 grams) and the product was filtrated, washed with dichloroethane (2×10 mL) and dried in cooling at ~5° C. The solid was filtered, washed with toluene and dried in vacuum to affords 5.11 grams BOS—Na, 98.5% purity on HPLC.

EXAMPLE 5

Preparation of Zonisamide from BOS—Na

In a 250 mL three necked flask, equipped with thermometer, mechanical stirrer and condenser was charged POCl$_3$ (60 mL) and BOS—Na (19 grams). The reaction mixture was heated to reflux and the reflux was maintained for three hours. The excess of POCl$_3$ was distilled and to the obtained residue was added ethyl-acetate. After a few minutes of stirring, the solids were filtered and washed with ethyl-acetate. The solution of ethyl-acetate contains the product 1,2-benzisoxazole methane sulfonyl chloride.

To the chilled solution of the product in ethyl-acetate (~5° C.), ammonia gas was bubbled until the solution reached pH 12. The solids were filtered and washed with ethyl-acetate. The combined solutions of ethyl-acetate were evaporated on rotovapor to afford the product zonisamide (14.88 grams).

Crystalline Forms of the Zonisamide Intermediate (BOS): Characterization

Novel Crystal Forms of BOS—Na

BOS—Na Monohydrate Novel Form I

BOS—Na novel form I was characterized by X-Ray Powder Diffraction (XRD), Furier Transform Infra Red Spectroscopy (FTIR), Differential Thermal Gravimetry (DTG), and Karl-Fischer titration (KF).

XRD

BOS—Na novel form I is characterized by the following X-Ray Diffraction main peaks at about 5.0, 15.7, 16.5, 17.3, 18.6, 19.1, 19.7, 21.5, 22.8, 23.2, 23.5 and 24.3±0.2 degrees two theta. The most characteristic XRD peaks at about 5.0, 17.3, 18.0, 18.6, 19.7±0.2 degrees two theta.

X-Ray Powder. Diffraction pattern is given in FIG. 1.

FTIR

FTIR spectrum of BOS—Na novel form I is characterized by the following peaks at about 3546, 3485, 3440, 1612, 1513, 1439, 1410, 1382, 1234, 1199, 1048, 918, 855, 760, 669 and 593 cm$^{-1}$. The most characteristic FTIR peaks at about 593, 669, 1641, 3440, 3485 and 3546 cm$^{-1}$.

Figure 2:
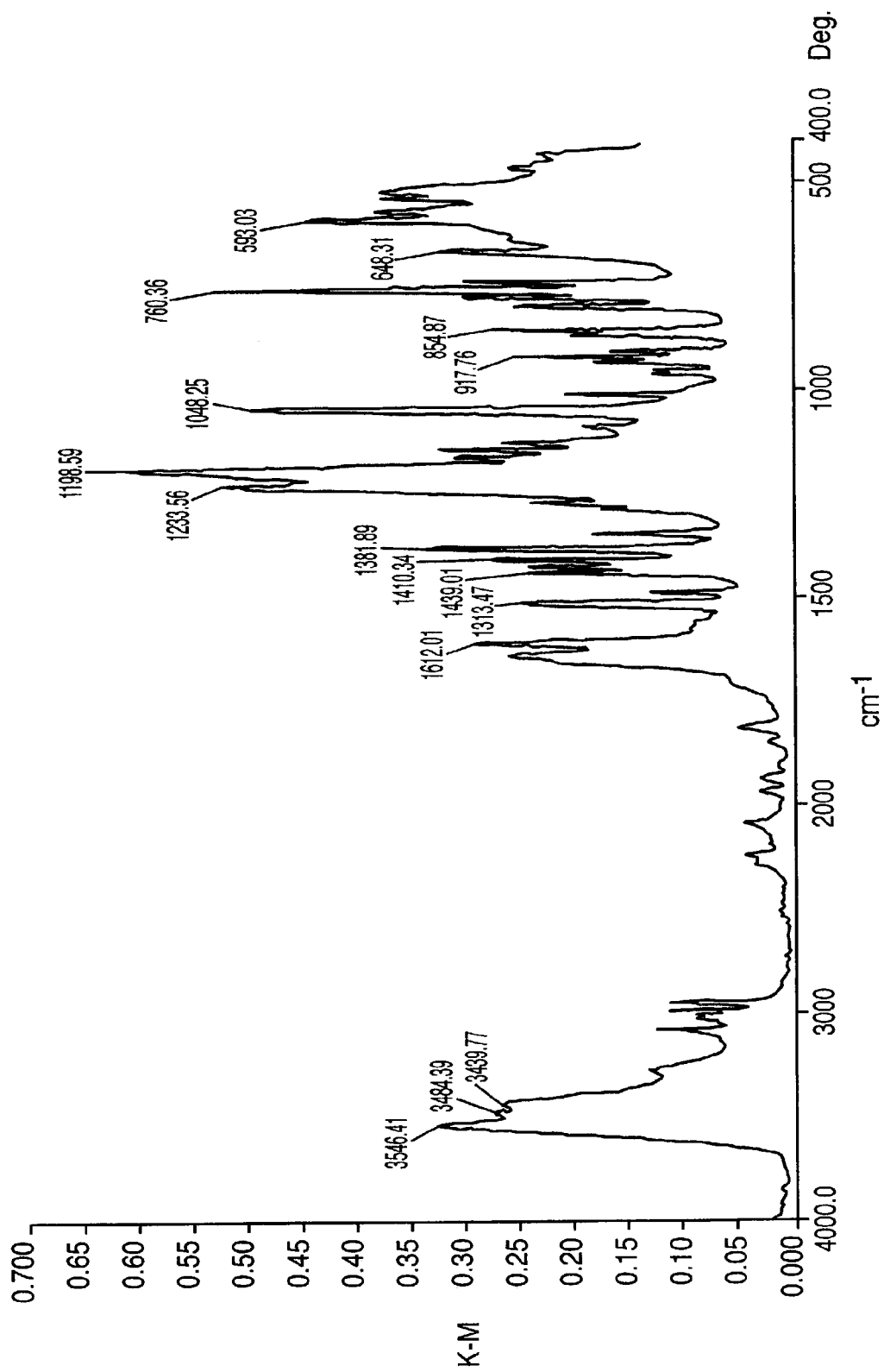
FIG. 2 depicts the Furier Transform Infra Red Spectroscopy (FTIR) spectrum of BOS—Na novel Form I.

FTIR spectrum of BOS—Na novel form I is given in FIG. 2.

DTG

The combined DTA and TGA profiles of Bos-Na form I is characterized by an endothermic peak at about 100° C. The TGA curve shows a weight loss step of about 7% in this temperature range. This weight loss step is due to water released out of the sample.

Figure 3:
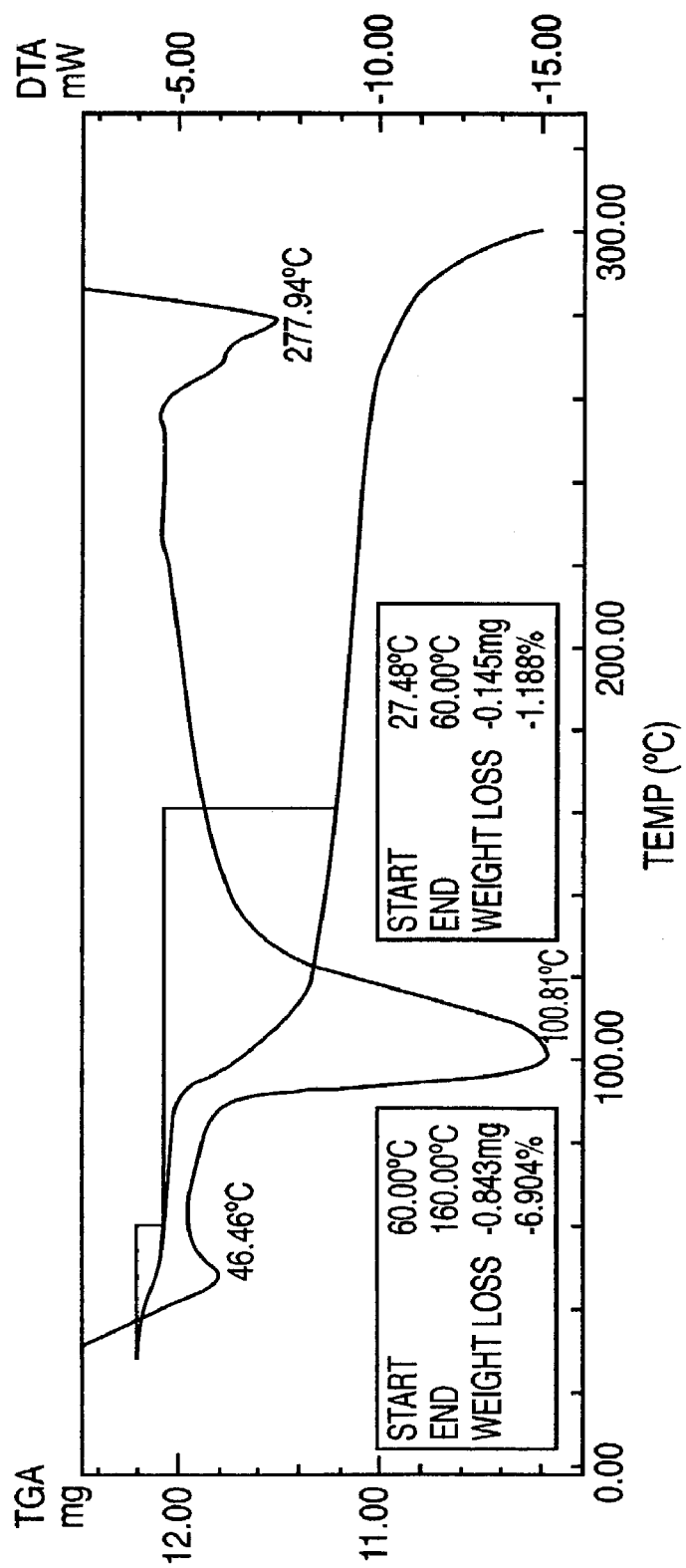
FIG. 3 depicts the Differential Thermal Gravimetry (DTG) of BOS—Na novel Form I.

DTG profile is given in FIG. 3.

KF

Water content measured by Karl-Fischer (KF) method is in agreement with TGA weight loss step and is about 7%. This water content is coincident with the expected water content of monohydrate.

BOS—Na Novel, Form II

BOS—Na novel form II was characterized by X-Ray Powder Diffraction (XRD), Furier Transform Infra Red Spectroscopy (FTIR) and Differential Thermal Gravimetry (DTG).

XRD

BOS—Na novel form II is characterized by the following X-Ray Diffraction main peaks at about 5.3, 15.9, 16.6, 21.3 and 26.7±0.2 degrees two theta. The most characteristic XRD peaks are at about 5.3, 16.6, 21.3, and 26.7±0.2 degrees two theta.

Figure 4:
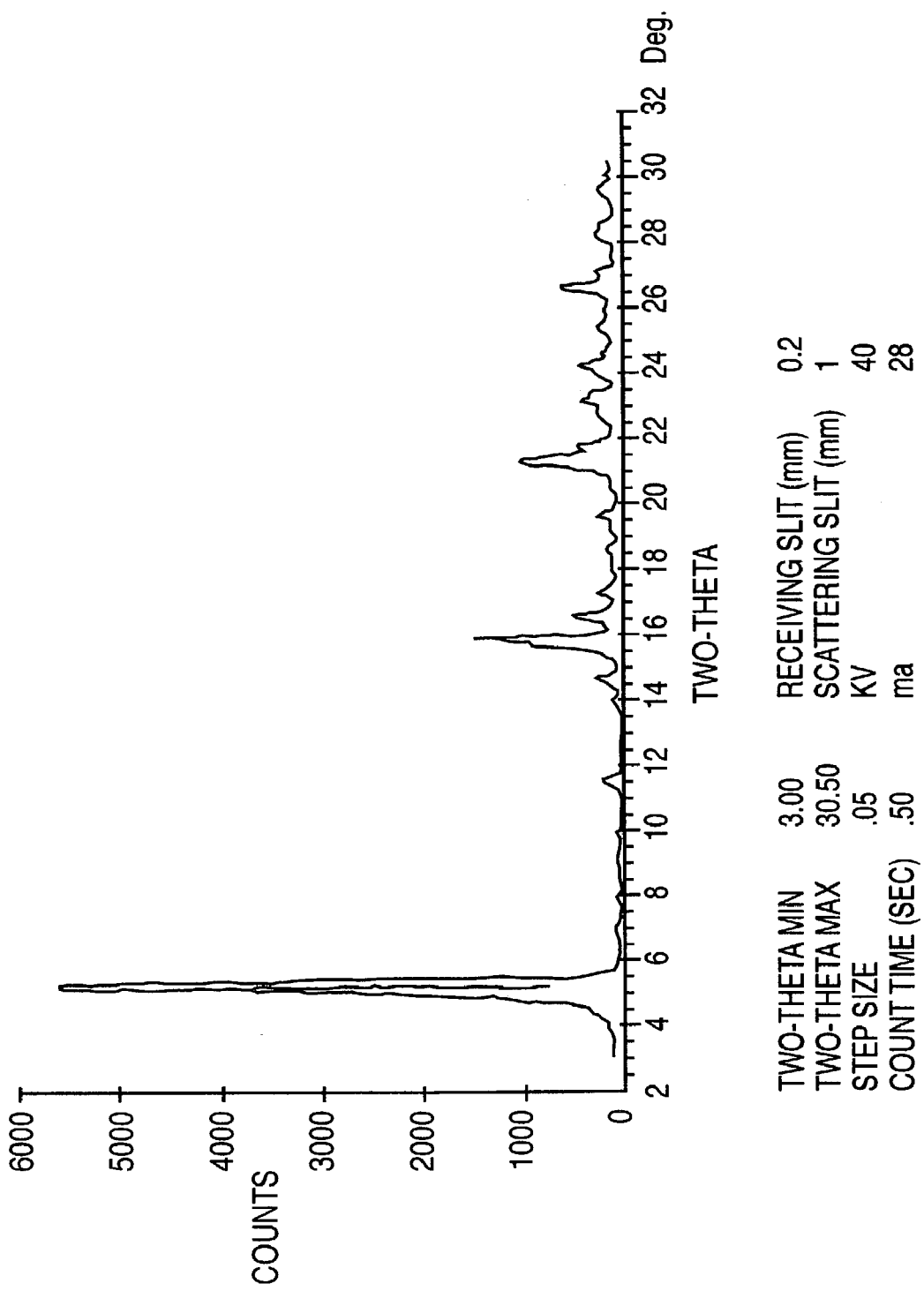
FIG. 4 depicts the X-ray Powder Diffraction (XRD) Pattern for BOS—Na novel Form II.

X-Ray Powder Diffraction pattern is given in FIG. 4.

FTIR

FTIR spectrum of BOS—Na novel form II is characterized by the following peaks at about 3597, 3535, 3496, 3067, 2998, 2951, 1606, 1516, 1438, 1382, 1213, 1064, 1055, 743, 663, 588, 541 and 522 cm$^{-1}$. The most characteristic FTIR peaks are at 3571 and 3597 cm$^{-1}$.

Figure 5:
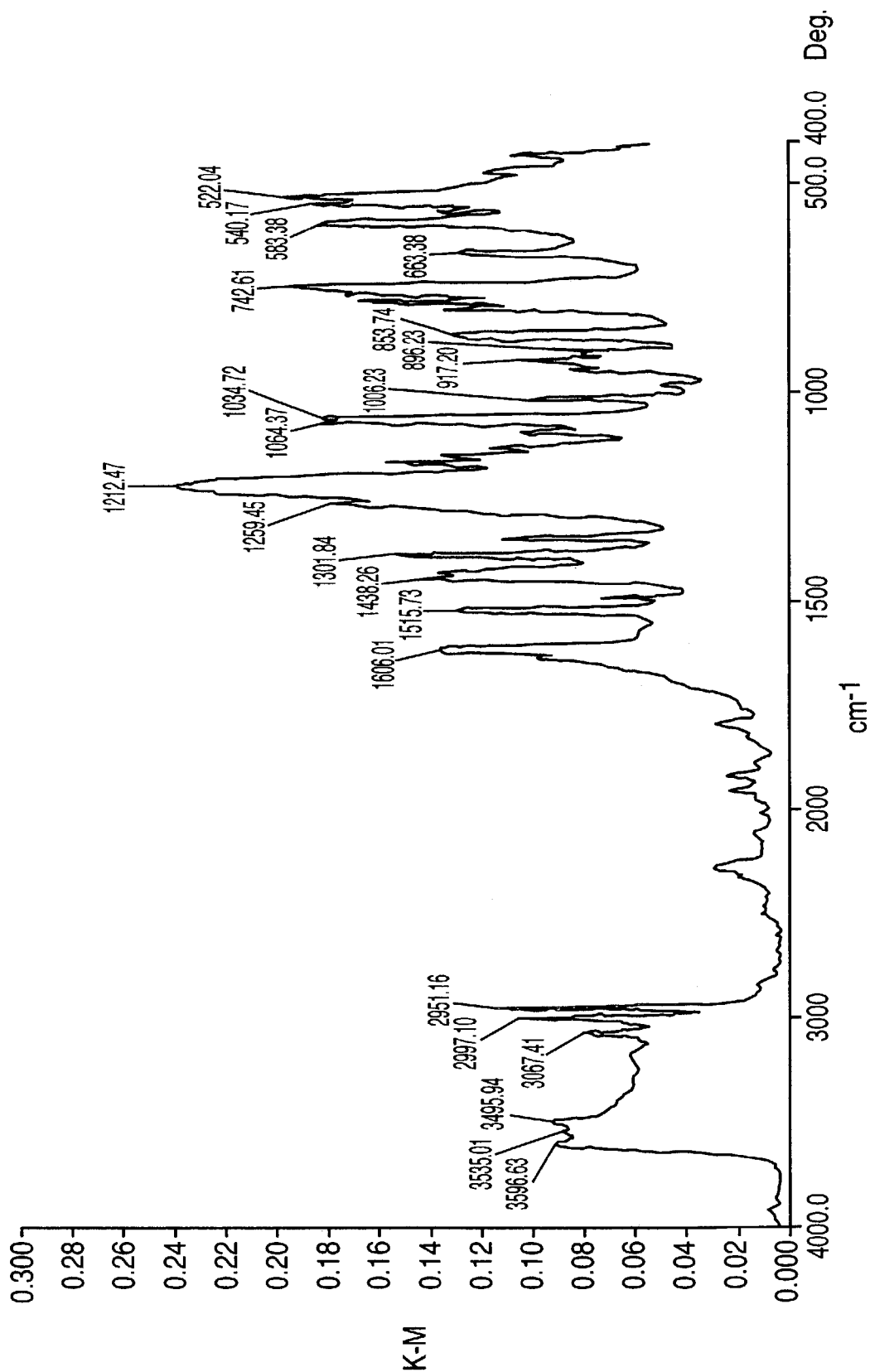
FIG. 5 depicts the Furier Transform Infra Red Spectroscopy (FTIR) spectrum of BOS—Na novel Form II.

FTIR spectrum of BOS—Na novel form II is given in FIG. 5.

DTG

Figure 6:
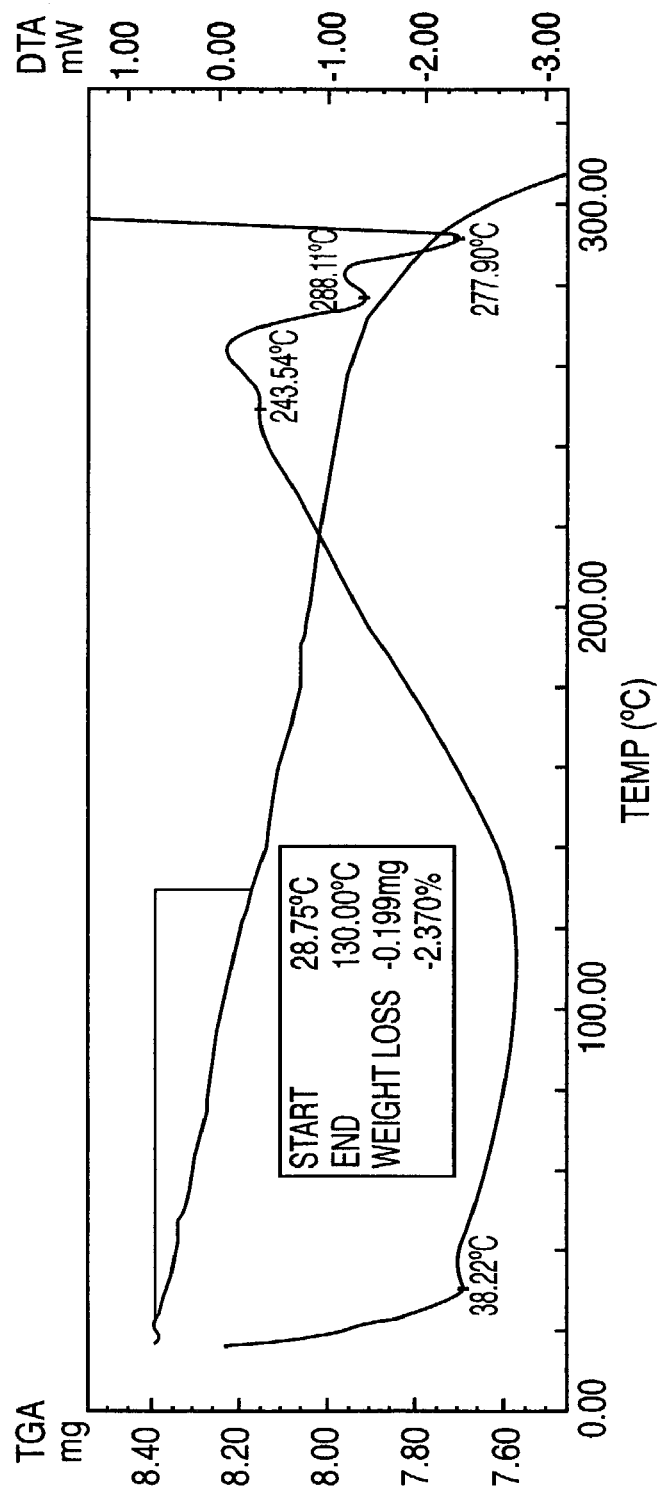
FIG. 6 depicts the Differential Thermal Gravimetry (DTG) of BOS—Na novel Form II.

DTG profile is given in FIG. 6.

DTG profile of BOS—Na novel form II is characterized by three endothermic peaks at about 243, 265 and 278° C. The sharp weight loss in this temperature range is due to decomposition of the sample.

BOS—Na Novel Form III

BOS—Na novel form III was characterized by X-Ray powder diffraction (XRD), Furier Transform Infra Red Spectroscopy (FTIR) and Differential Thermal Gravimetry (DTG).

XRD

BOS—Na novel form III is characterized by the following X-Ray Diffraction main peaks at about 5.0, 5.3, 15.7, 17.8 and 21.4±0.2 degrees two theta. The most characterisitc XRD peaks are at about 5.0, 5.3, and 17.8±0.2 degrees two theta.

Figure 7:
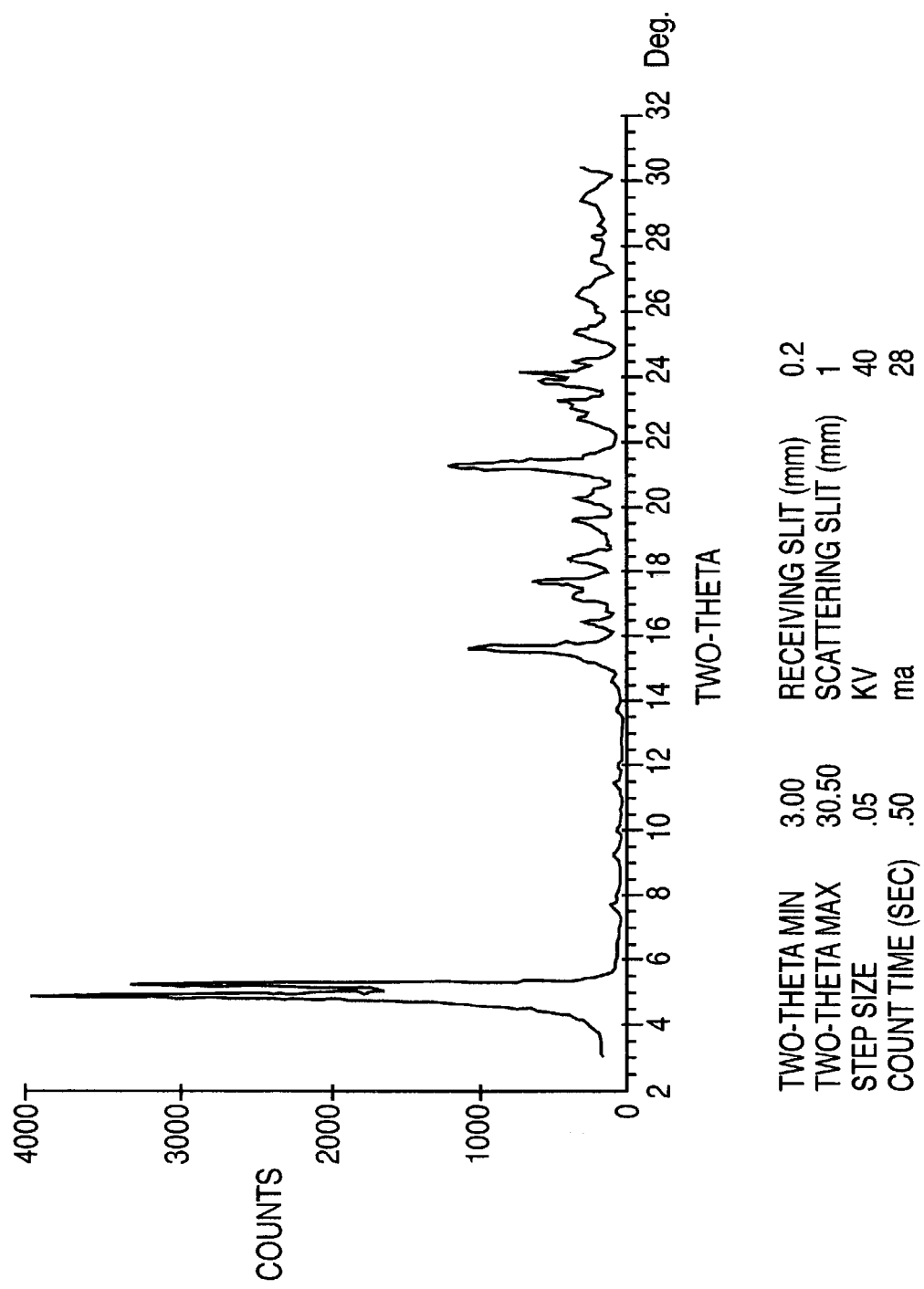
FIG. 7 depicts the X-ray Powder Diffraction (XRD) Pattern for BOS—Na novel Form III.

X-Ray Powder Diffraction pattern is given in FIG. 7.

FTIR

FTIR spectrum of BOS—Na novel form III is characterized by the following peaks at about 3604, 3495, 3067, 2998, 2951, 1605, 1516, 1438, 1382, 1215, 1136, 1065, 1052, 777, 747, 696, 588 and 521 $cm^{-1}$. The most characteristic FTIR peaks are at about 696, 812, 1065 and 3604 $cm^{-1}$.

Figure 8:
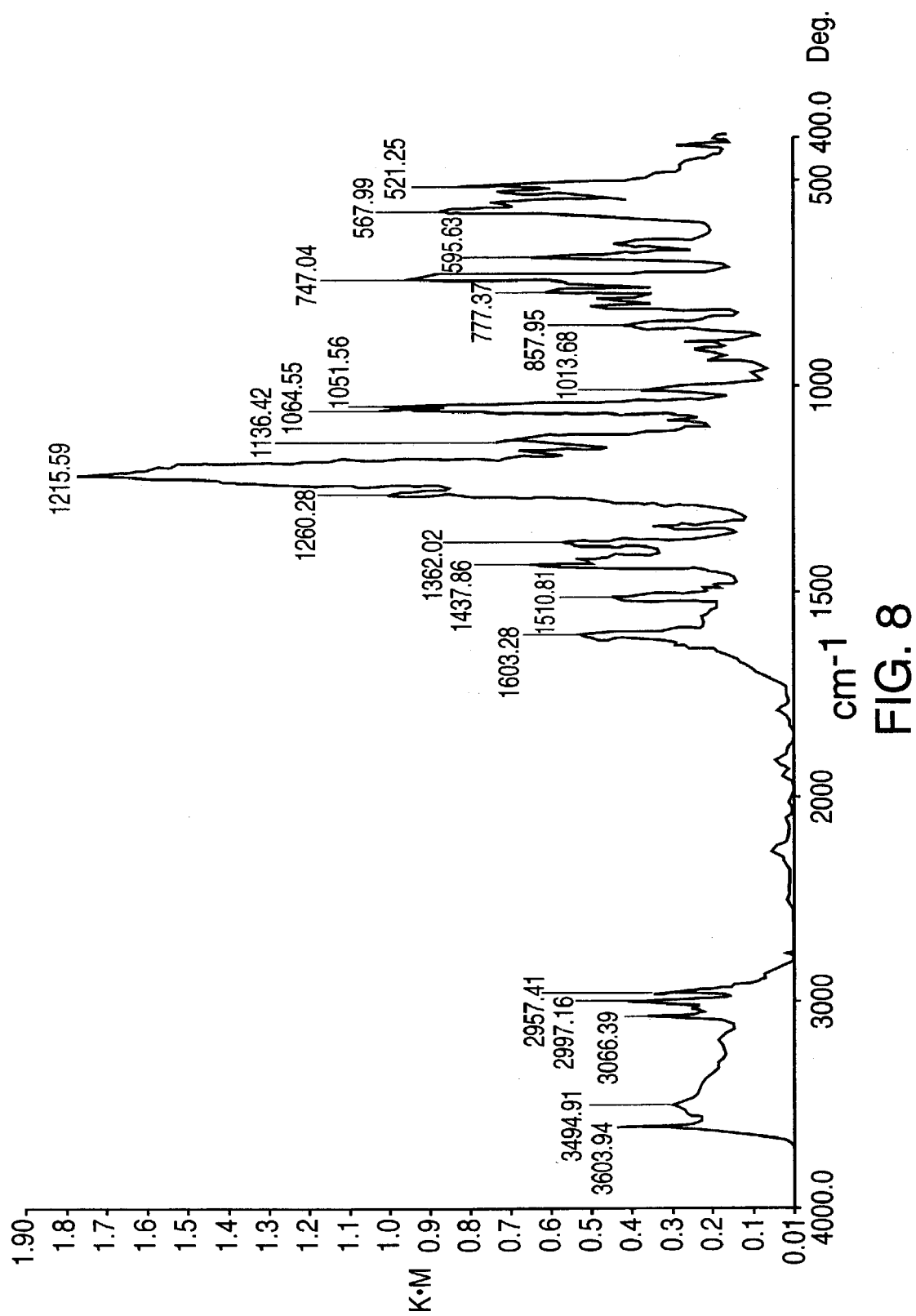
FIG. 8 depicts the Furier Transform Infra Red Spectroscopy (FTIR) spectrum of BOS—Na novel Form III.

FTIR spectrum of BOS—Na novel form III is given in FIG. 8.

DTG

Figure 9:
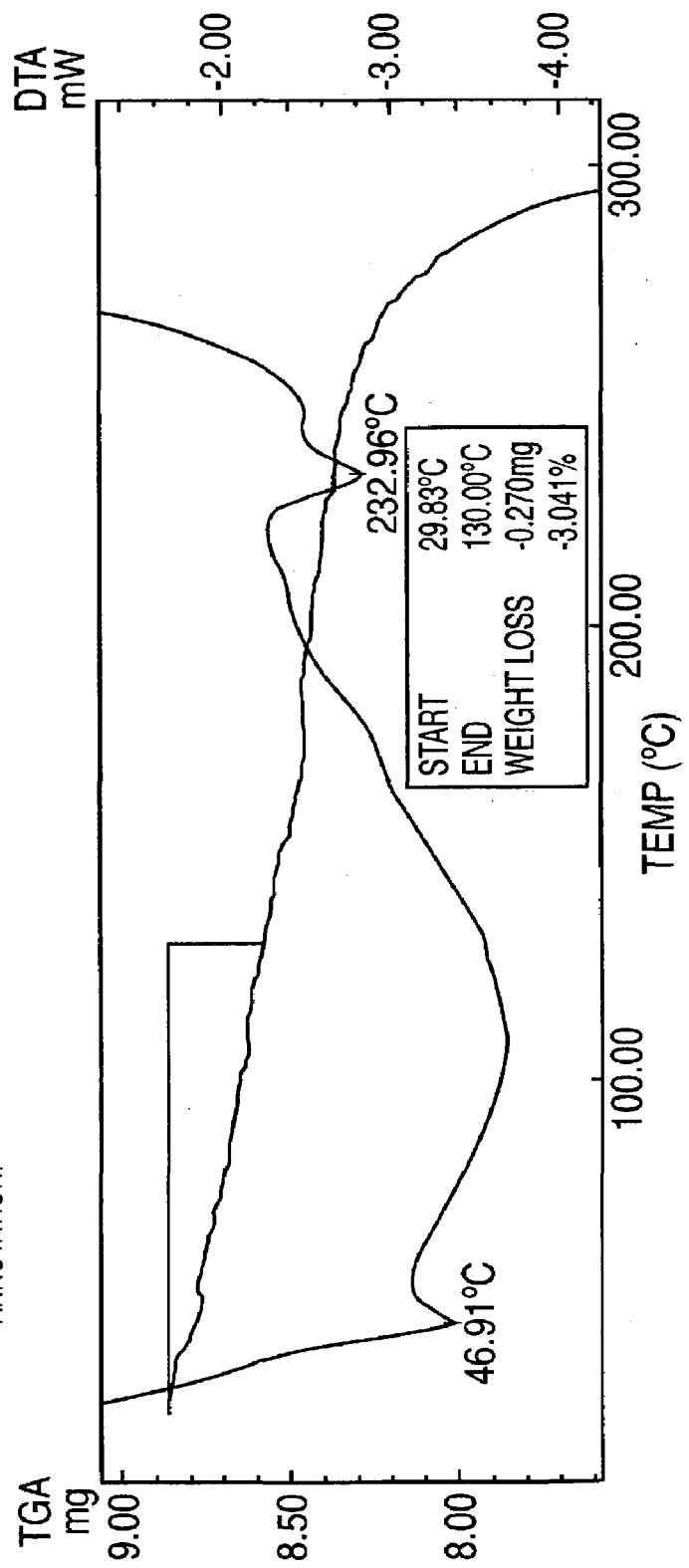
FIG. 9 depicts the Differential Thermal Gravimetry (DTG) of BOS—Na novel Form III.

DTG profile is given in FIG. 9.

DTG profile of BOS—Na novel form III is characterized by an endothermic peak at about 233° C. The sharp weight loss in this temperature range is due to decomposition of the sample.

BOS—Na Novel Form IV

BOS—Na novel form IV was characterized by X-Ray Powder Diffraction (XRD), Furier Transform Infra Red Spectroscopy (FTIR), Differential Thermal Gravimetry (DTG) and Karl-Fischer titration (KF).

XRD

BOS—Na novel form IV is characterized by the following X-Ray Diffraction main peaks at about 4.5, 5.9, 8.8, 11.3, 16.3, 19.0, 22.5, 23.9, 24.7, 25.0, 26.8, 28.1, 29.7, 30.9, 32.6, 33.6, 35.5, 36.6±0.2 degrees two theta.

Figure 10:
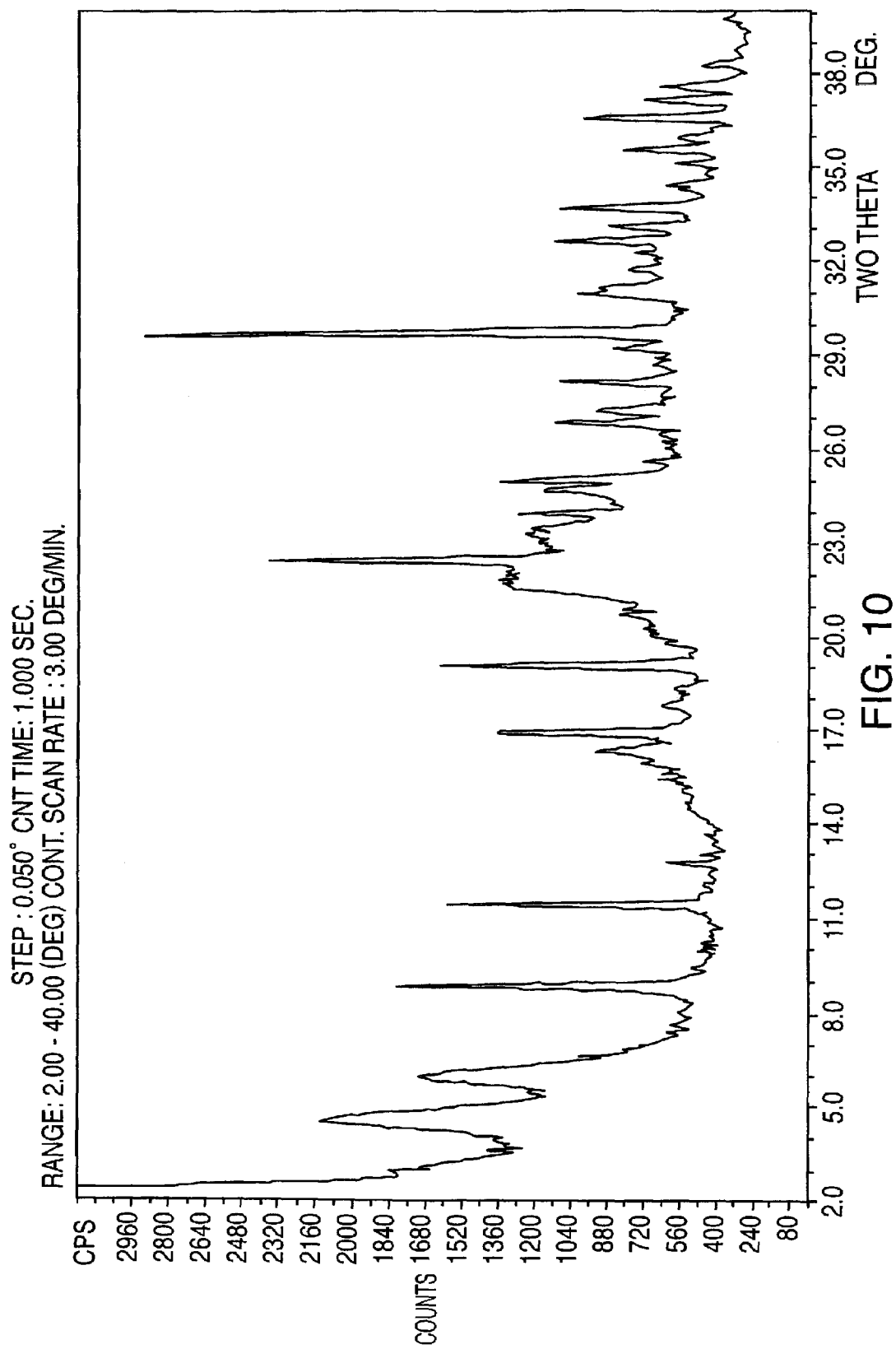
FIG. 10 depicts the X-ray Powder Diffraction (XRD) Pattern for BOS—Na novel Form IV.

X-Ray Powder Diffraction pattern is given in FIG. 10.

FTIR

FTIR spectrum of BOS—Na novel form IV is characterized by the following peaks at about 3431, 1567, 1416, 924, 862, and 586 $cm^{-1}$.

Figure 11:
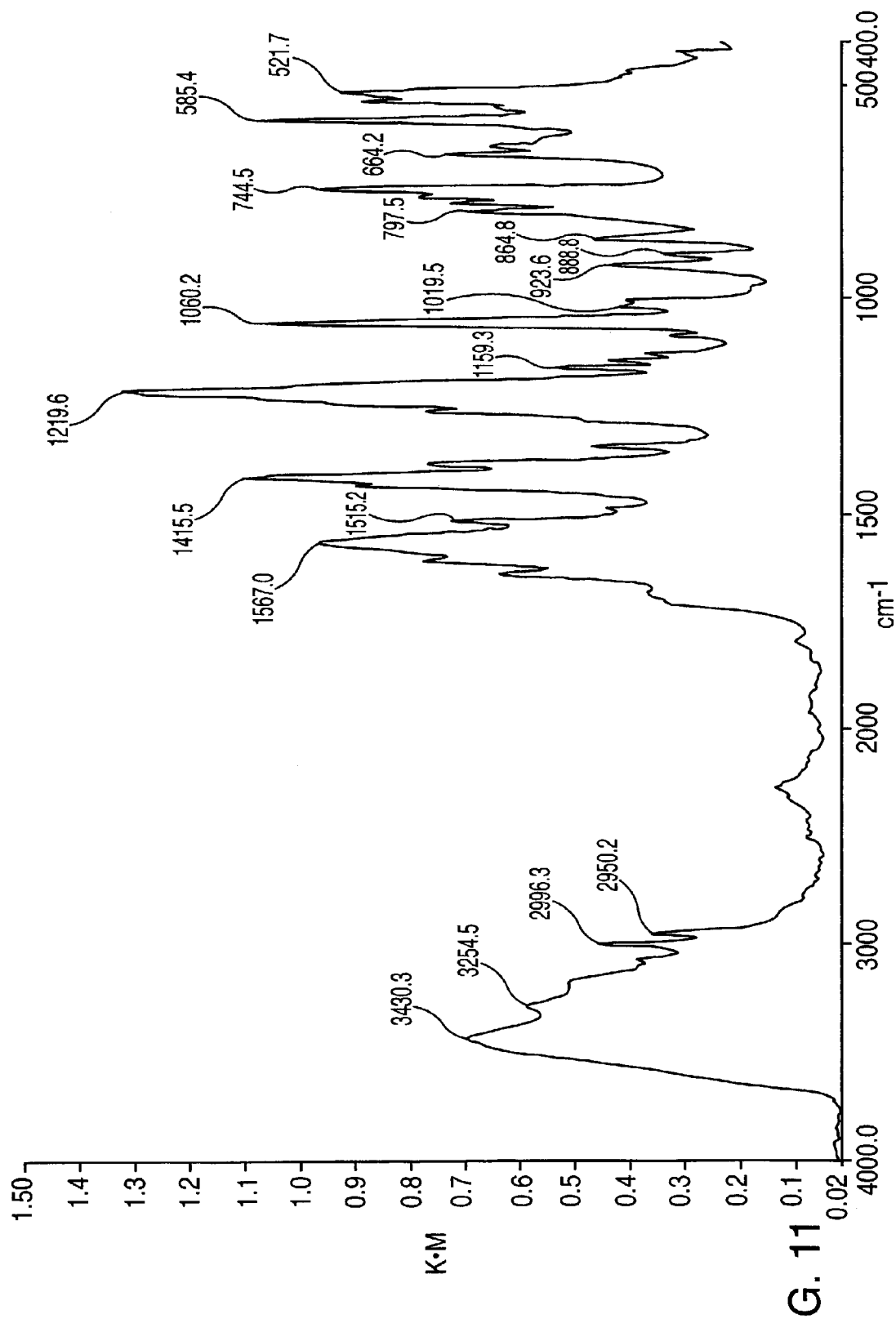
FIG. 11 depicts the Furier Transform Infra Red Spectroscopy (FTIR) spectrum of BOS—Na novel Form IV.

FTIR spectrum,of BOS—Na novel form IV is given in FIG. 11.

DTG

DTG profile is characterized by an endothermic peak at about 50° C. and a weight loss step of about 2.9%. This LOD value is in agreement with the water content determined by KF.

Figure 12:
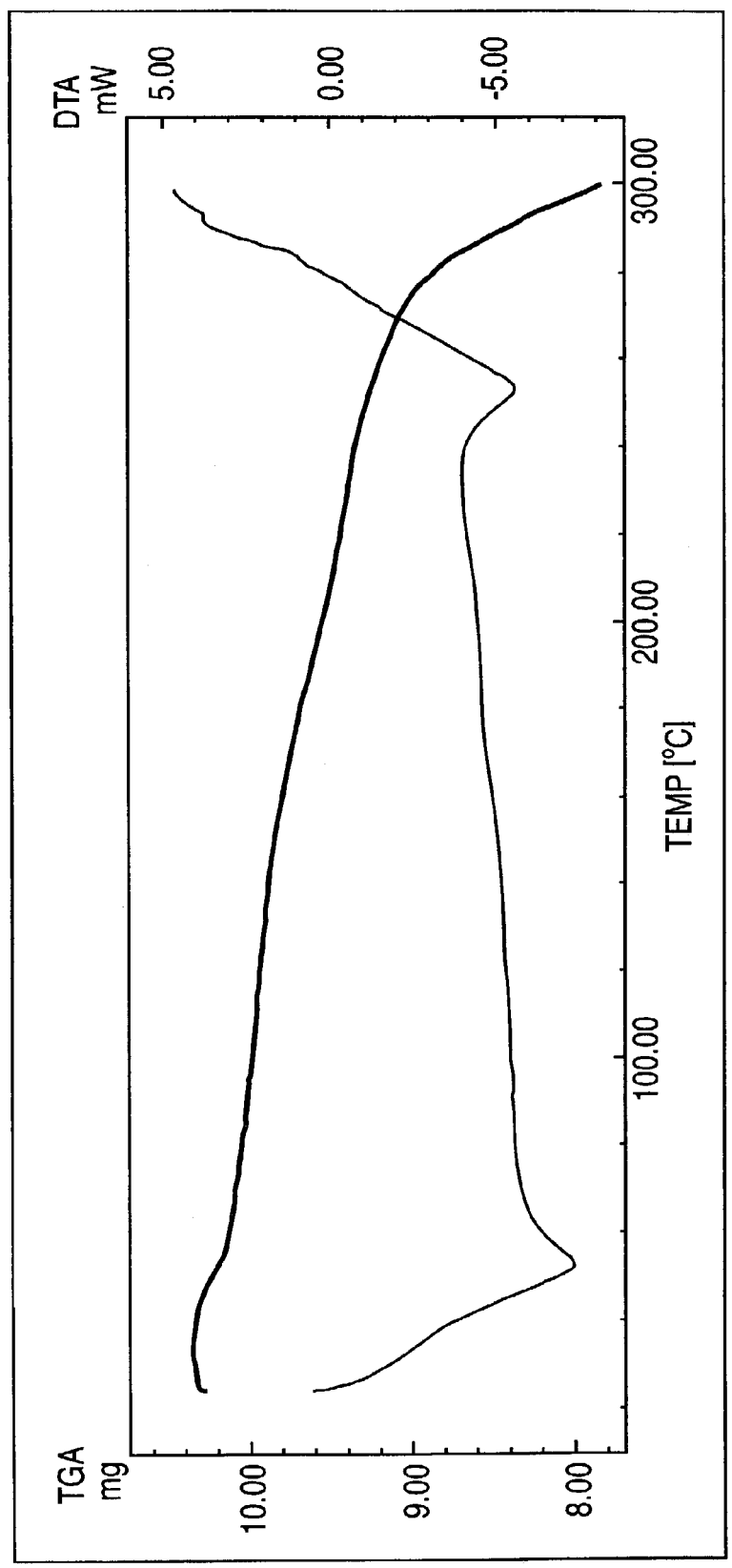
FIG. 12 depicts the Differential Thermal Gravimetry (DTG) of BOS—Na novel Form IV.

DTG profile is given in FIG. 12.

BOS—Na Novel Form V

BOS—Ba novel form V was characterized by X-Ray Powder Diffraction (XRD), Furier Transform Infra Red Spectroscopy (FTIR), Differential Scanning Calorimetry, and Thermal Gravimetric Analysis (TGA).

XRD

XRD analysis were performed X-Ray powder diffractometer, Scintag, variable goniometer, Cu-tube, solid state detector. Sample holder: A round standard aluminum sample holder with round zero background quartz plate. Scanning parameters: Range: 2–40 degrees two theta. Continuous scan rate: 3 deg./min.

BOS—Na novel form V is characterized by the following X-Ray Diffraction main peaks at about 6.7, 10.9, 16.2, 21.0, 21.2 and 22.2±0.2 degrees two theta.

Figure 13:
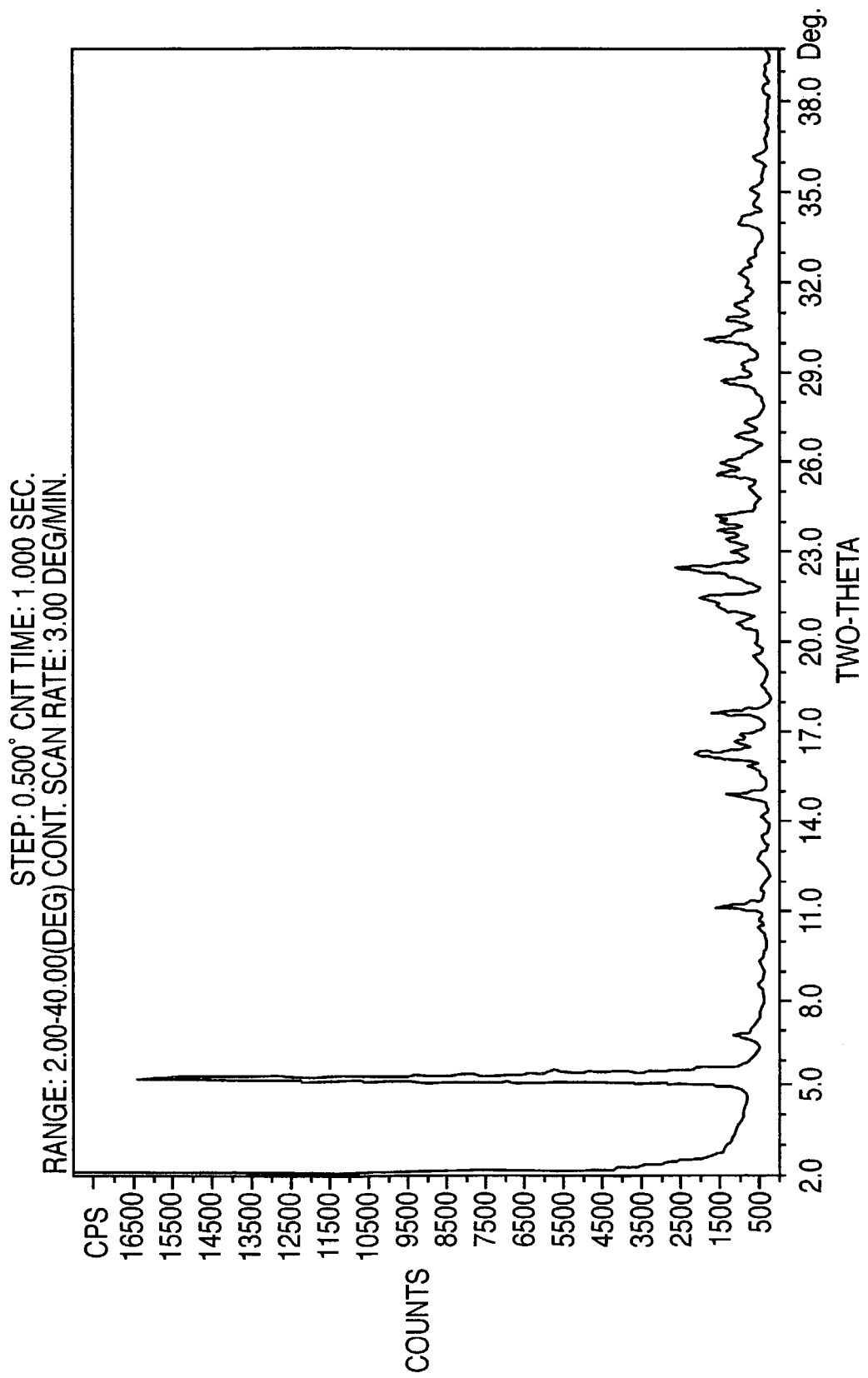
FIG. 13 depicts the X-ray Powder Diffraction (XRD) Pattern for BOS—Na novel Form V.

X-Ray Powder Diffraction pattern is given in FIG. 13.

FTIR

FTIR spectrum was collected on Perkin-Elmer Spectrum One FTIR spectrometer using Diffused Reflectance technique. Scanning range: 400–4000 $cm^{-1}$, number of scans: 16, resolution: 4.0 $cm^{-1}$.

FTIR spectrum of BOS—Na novel form V is characterized by the following peaks at about 3601, 3520, 1587, 1055, 793 and 753 $cm^{-1}$.

Figure 14:
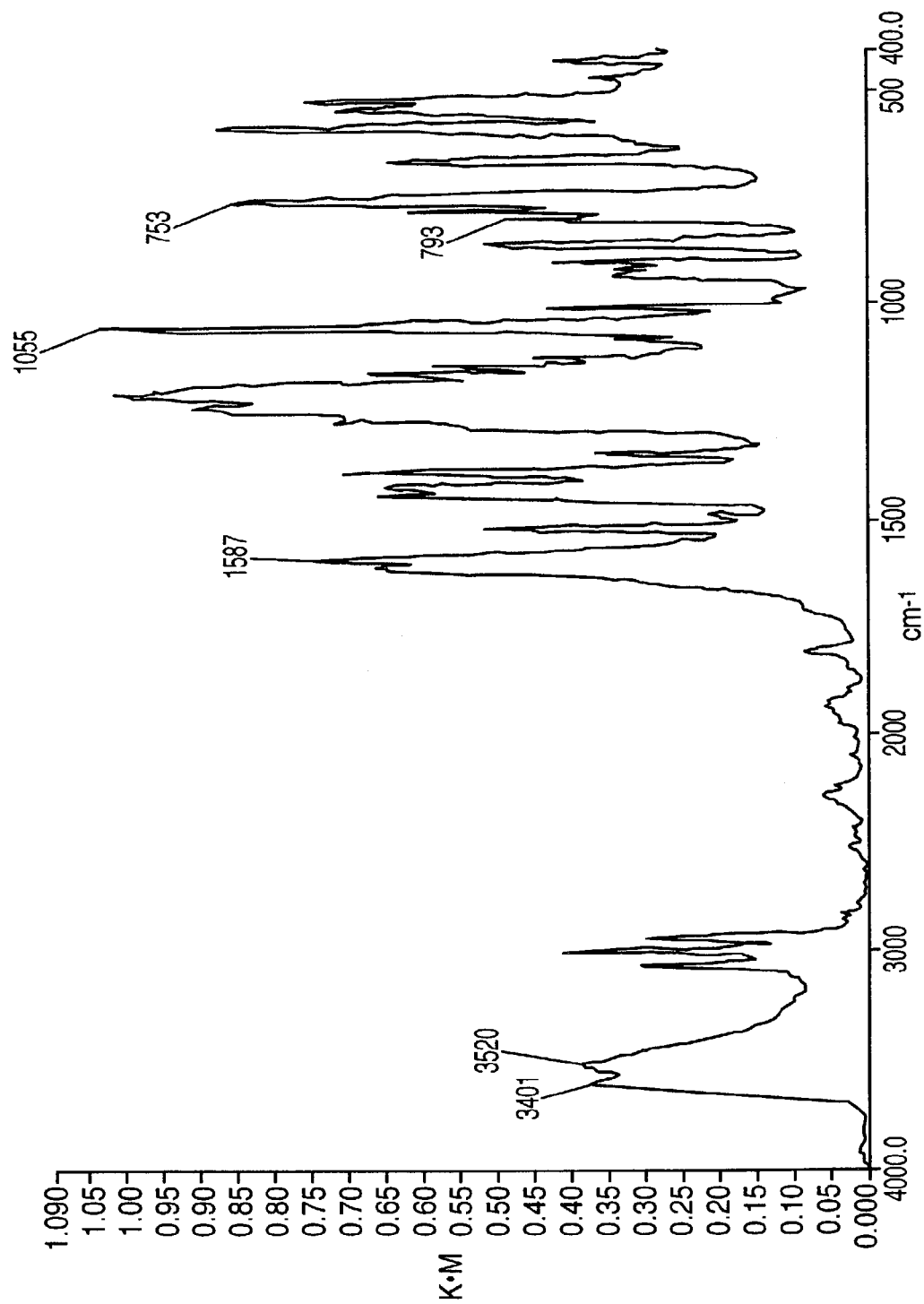
FIG. 14 depicts the Furier Transform Infra Red Spectroscopy (FTIR) spectrum of BOS—Na novel Form V.

FTIR spectrum of BOS—Na novel form V is given in FIG. 14.

DSC

DSC 821$^e$, Mettler Toledo instrument was used for the DSC analysis. Sample weight: 3–5 mg. Heating rate: 10° C./min. Number of holes in the crucible:3.

DSC profile is characterized by two overlapped endothermic peaks at about 164° C.

Figure 15:
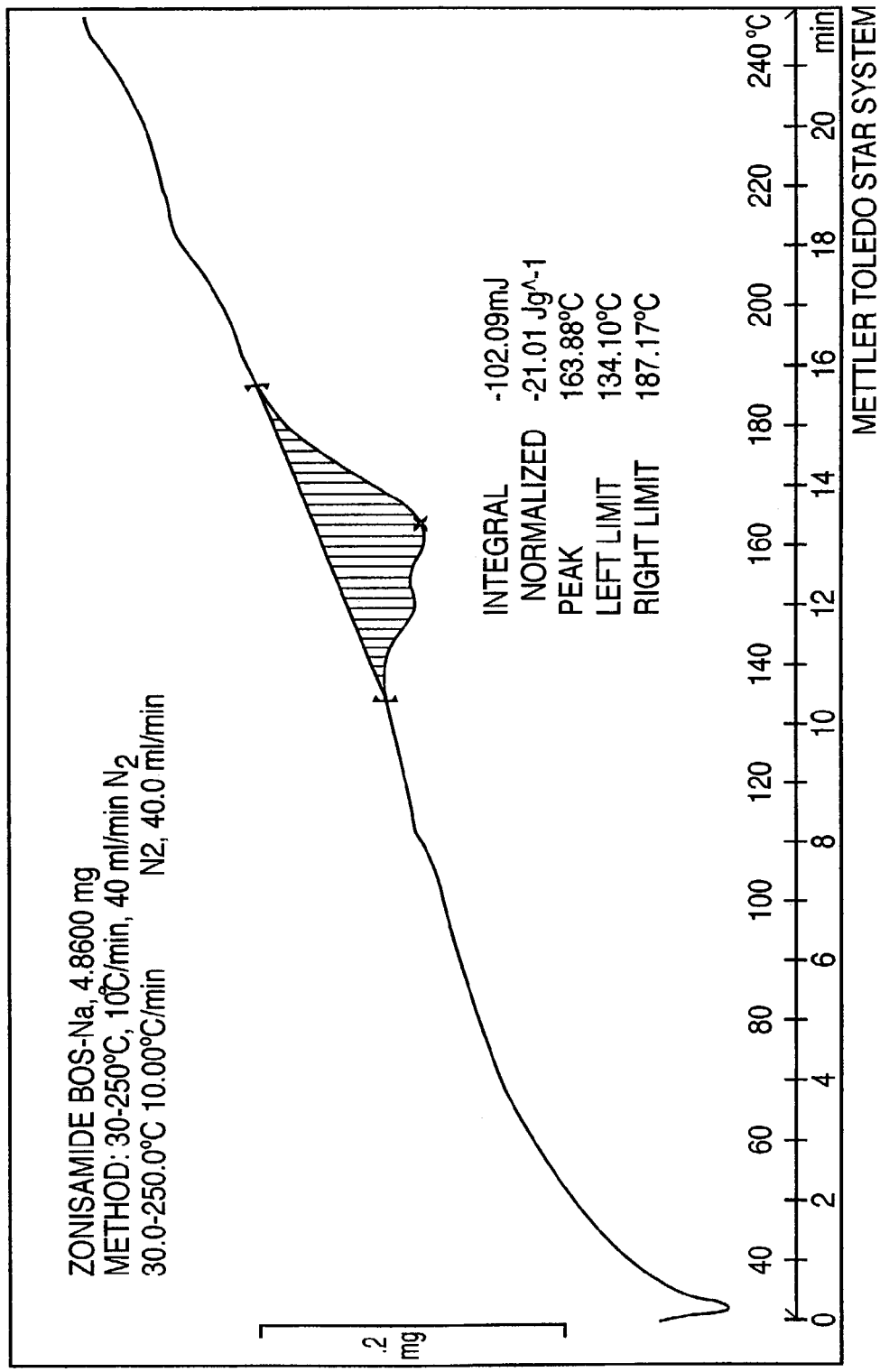
FIG. 15 depicts the Differential Scanning Calorimetry (DSC) of BOS—Na novel Form V.

DSC profile of BOS—Na noevl form V is given in FIG. 15.

TGA

Mettler TG50 instrument was used for the TGA analysis. Heating rate: 10° C./min. Nitrogen flow: 40 ml/min.

TGA thermogram shows LOD value of about 2% in a temperature range of up to 190° C.

Figure 16:
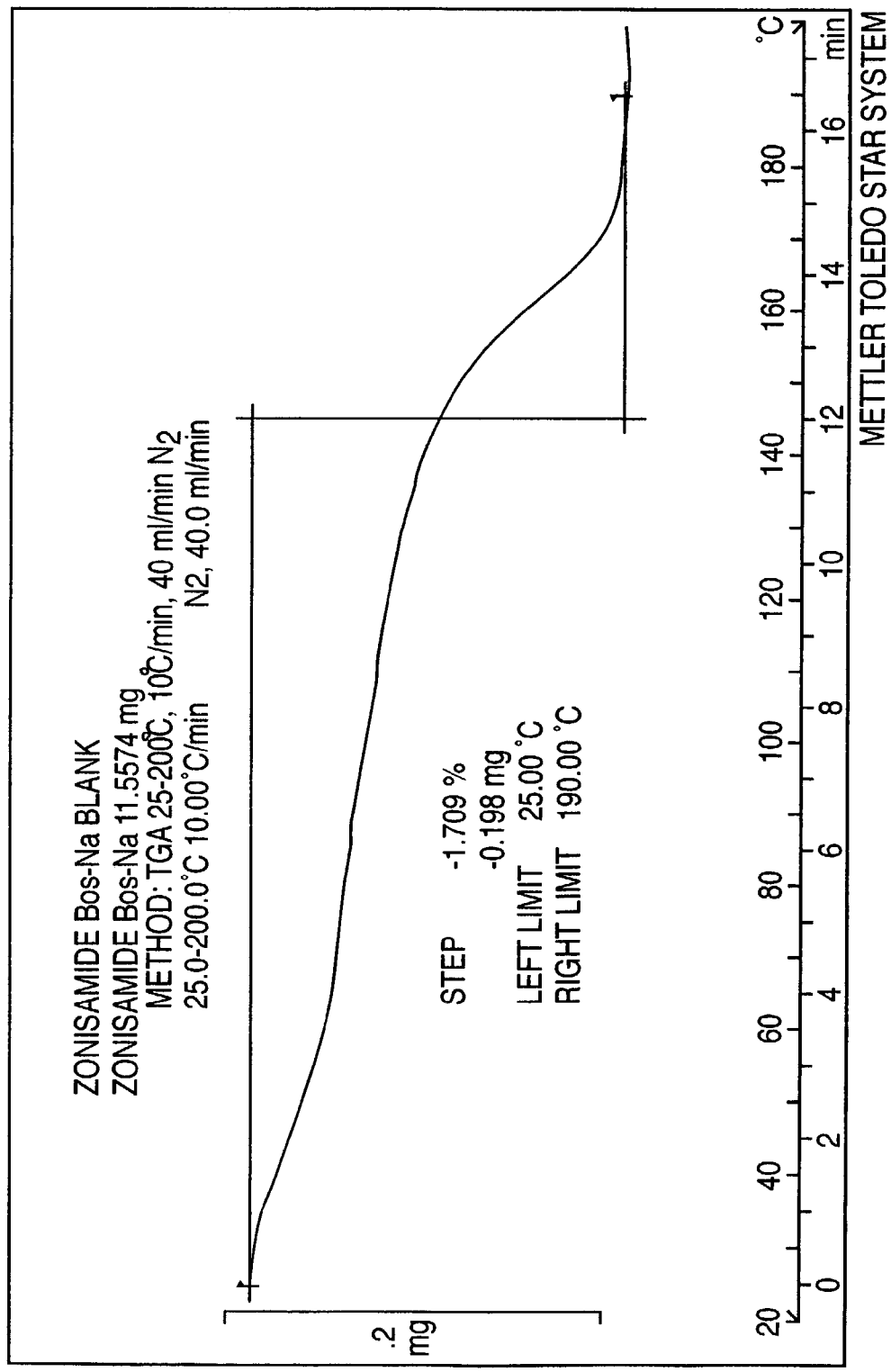
FIG. 16 depicts the Thermal Gravimetric Analysis (TGA) thermogram of BOS—Na novel Form V.

TGA thermogram of BOS—Na form V is given in FIG. 16.

Novel Crystal Form of BOS—Ba

BOS—Ba Novel Form I

BOS—Ba novel form I was characterized by X-Ray Powder Diffraction (XRD), Furier Transform Infra Red Spectroscopy (FTIR) and by Differential Thermal Gravimetry (DTG).

XRD

BOS—Ba novel form I is characterized by the following X-Ray Diffraction main peaks at about 5.2, 10.4, 12.0, 13.8, 15.6, 17.0, 23.9 and 25.4±0.2 degrees two theta.

Figure 17:
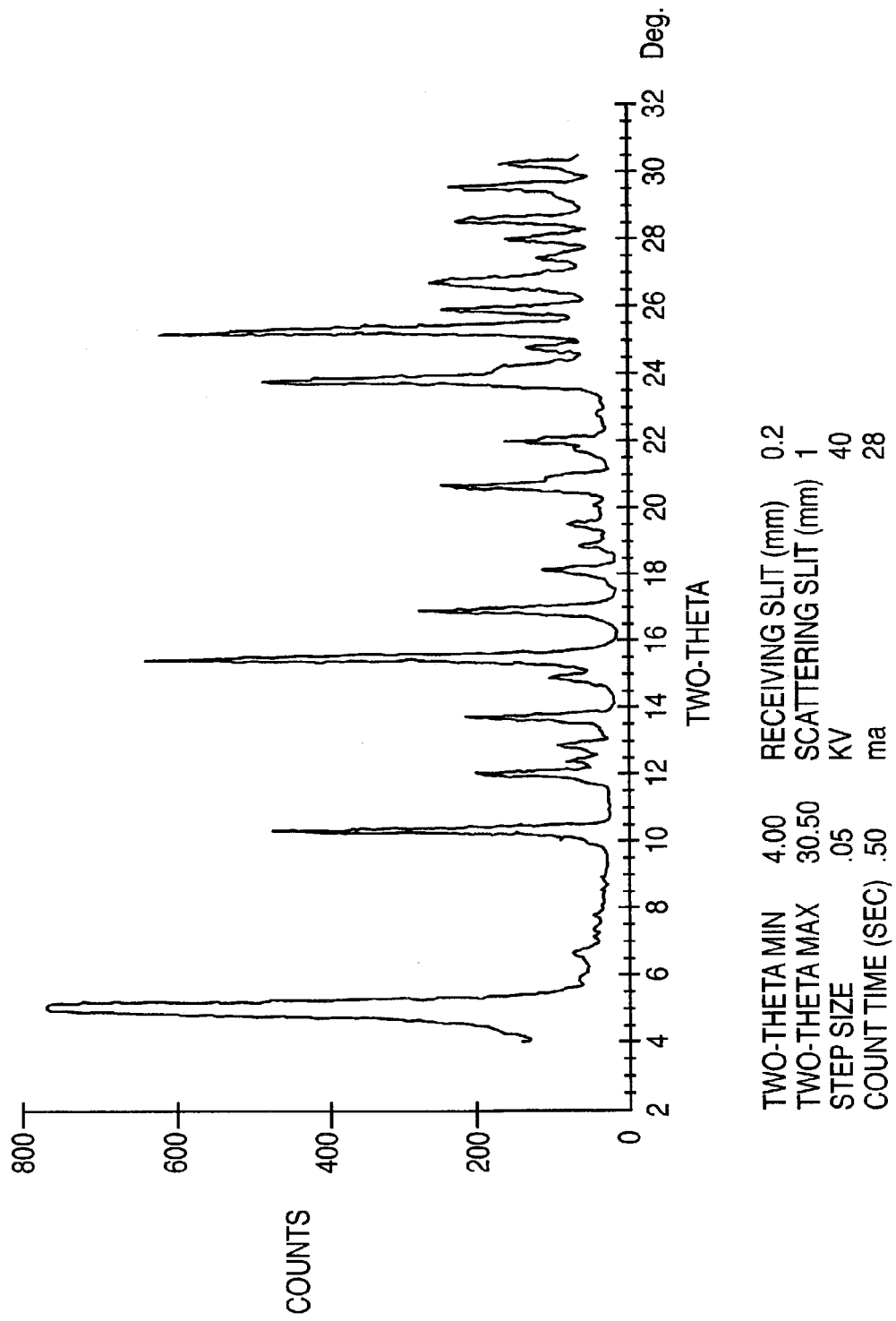
FIG. 17 depicts the X-ray Powder Diffraction (XRD) Pattern for BOS—Ba novel Form I.

X-Ray Powder Diffraction pattern is given in FIG. 17.

FTIR

FTIR spectrum of BOS—Ba is characterized by the following peaks at about 3544, 3491, 2985, 2943, 1626, 1610, 1509, 1437, 1383, 1369, 1223, 1209, 1175, 1153, 1055, 1043, 911, 869, 752, 651, 603, 543 and 511 $cm^{-1}$.

FTIR spectrum is given in FIG. 15.

DTG

DTG profile of BOS—Ba novel form I is characterized by an endothermic peak at about 200° C. A weight loss step of about 3.5% is observed in this temperature range.

Figure 18:
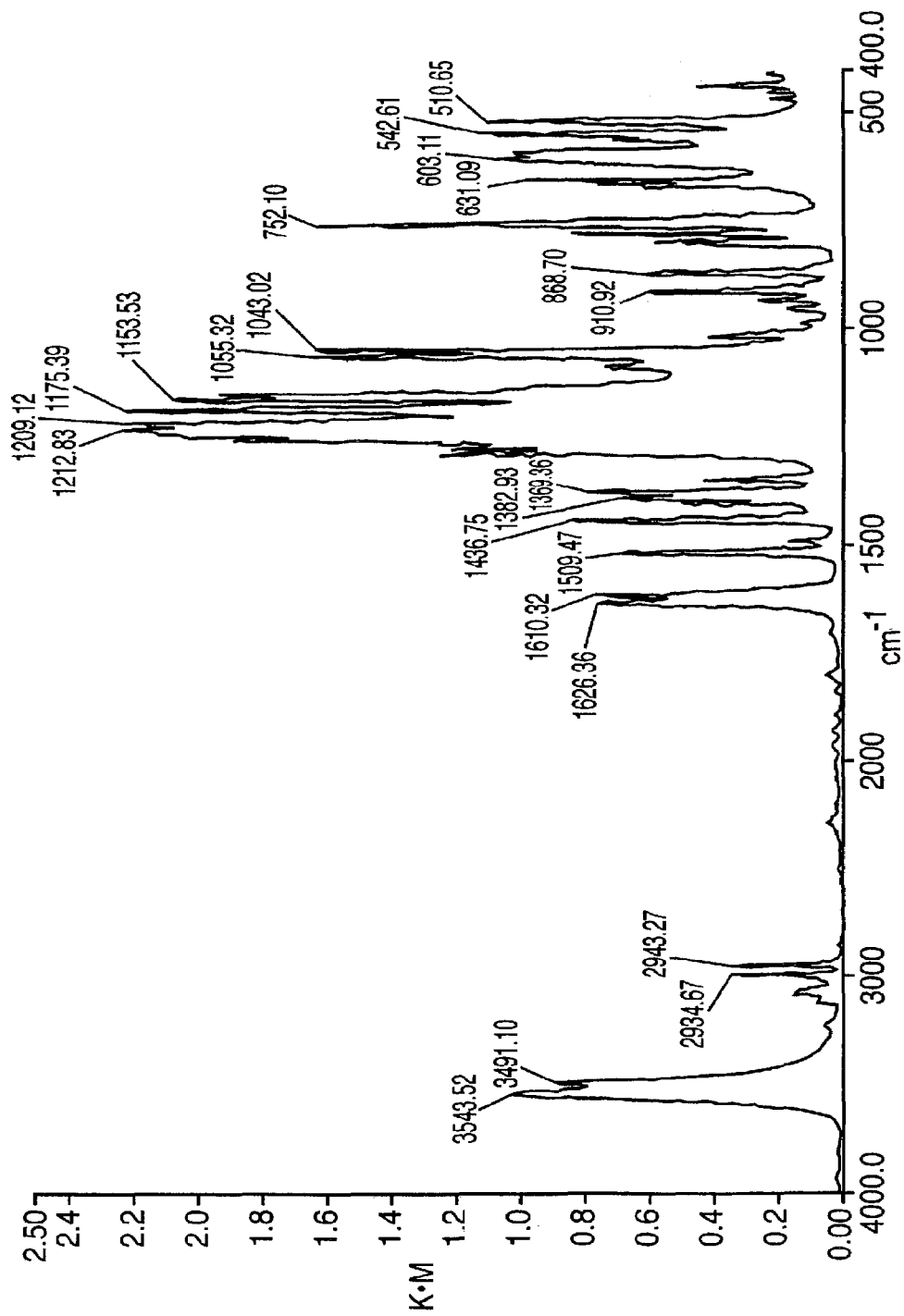
FIG. 18 depicts the Furier Transform Infra Red Spectroscopy (FTIR) spectrum of BOS—Ba novel Form I.

DTG thermogram of BOS—Ba novel form I is given in FIG. 18.

Novel Crystal Form of BOS—Ca

BOS—Ca Novel Form I

BOS—Ca novel form I was characterized by X-Ray Powder Diffraction (XRD) and by Differential Thermal Gravimetry (DTG).

XRD

BOS—Ca novel form I is characterized by the -following X-Ray Diffraction main peaks at about 5.4, 11.7, 16.0, 16.7, 17.7, 18.1, 19.1, 20.8, 24.5, 24.9 and 29.2±0.2 degrees two theta.

Figure 19:
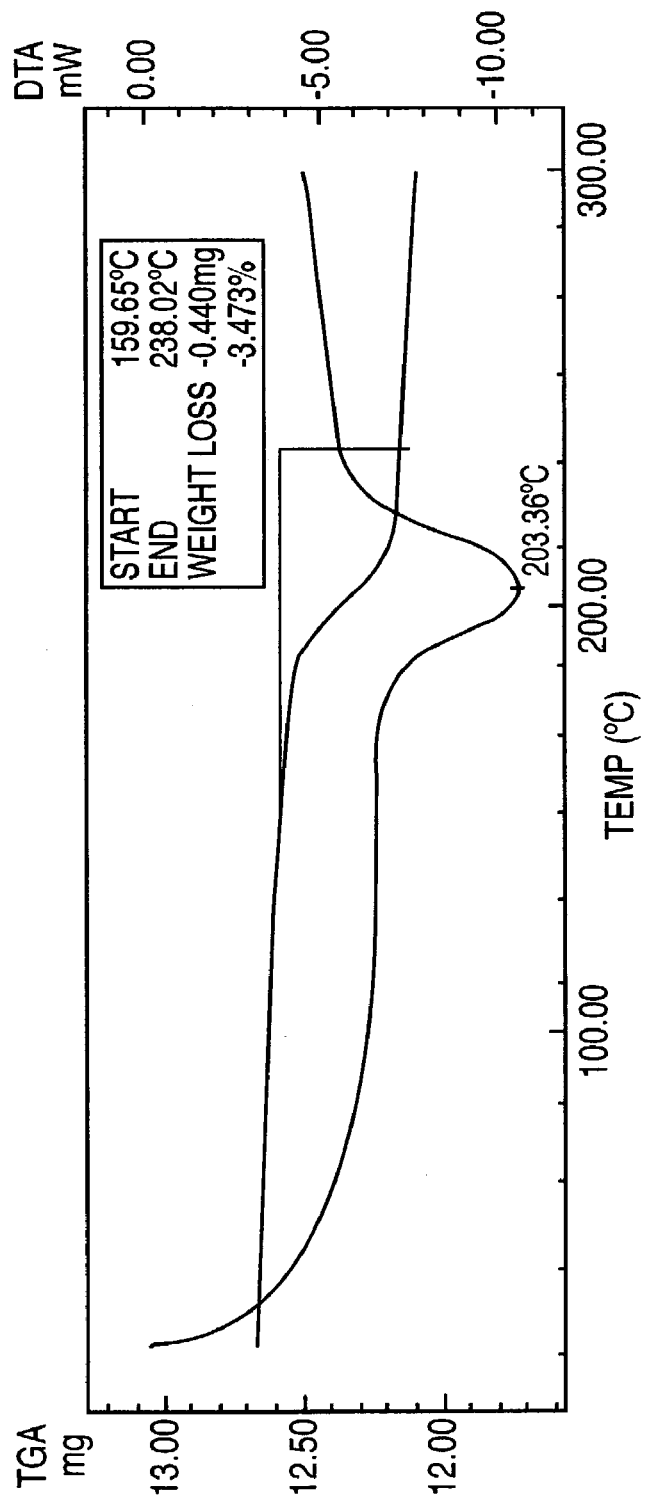
FIG. 19 depicts the Differential Thermal Gravimetry (DTG) of BOS—Ba novel Form I.

X-Ray Powder Diffraction pattern is given in FIG. 19.

DTG

DTG profile of BOS—Ca novel form I is characterized by two endothermic peaks at about 137 and 165° C. The LOD up to 200° C. is about 7.6%.

Figure 20:
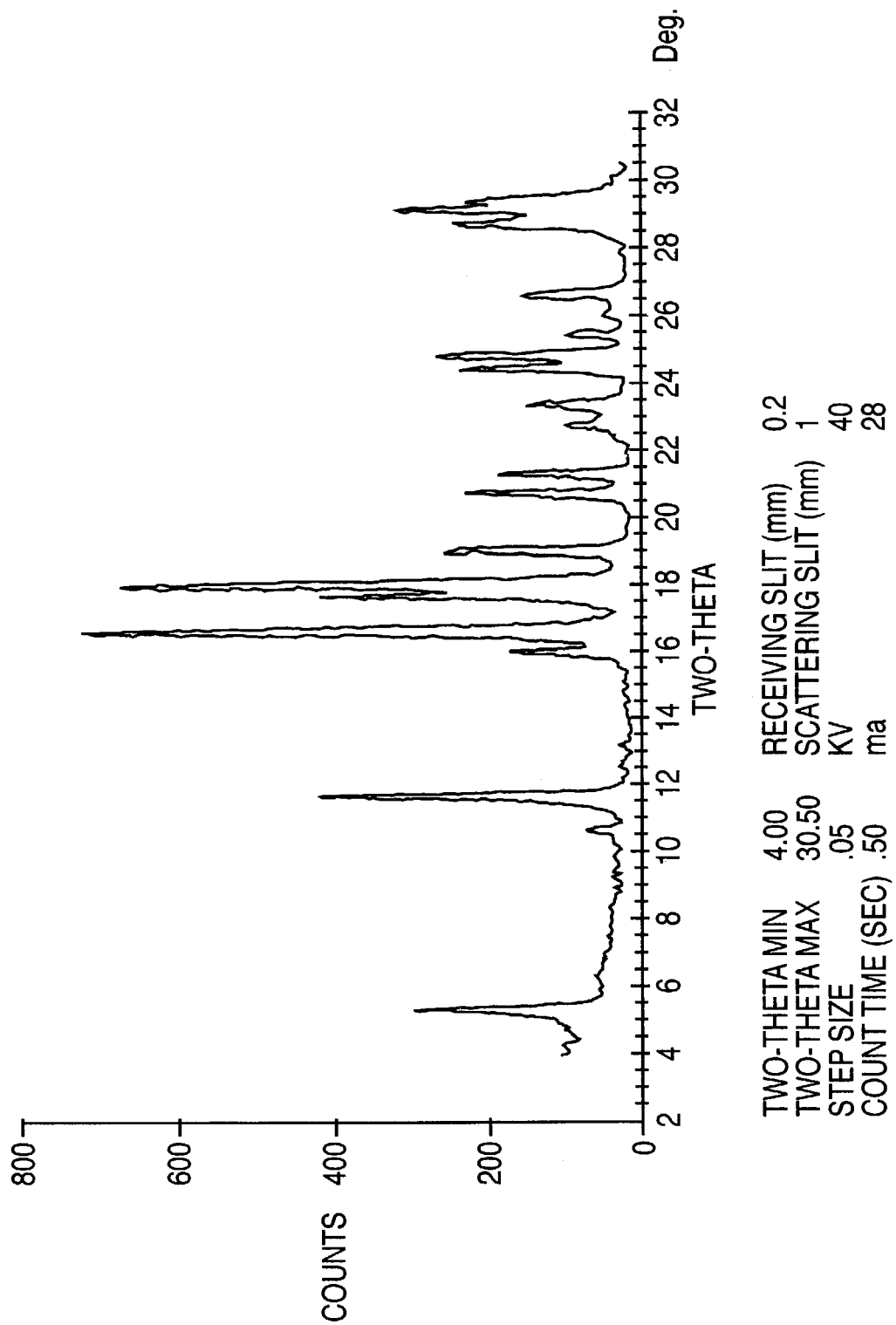
FIG. 20 depicts the X-ray Powder Diffraction (XRD) Pattern for BOS—Ca novel Form I.

DTG themogram of BOS—Ca novel form I is given in FIG. 20.

Novel Crystal Form of BOS—H

BOS—H Novel Form I

BOS—H monohydrate novel form I was characterized by X-Ray Powder Diffraction (XRD), by Differential Thermal Gravimetry (DTG) and by Karl-Fischer titration (KF).

XRD

BOS—H novel monohydrate novel form I is characterized by the following X-Ray Diffraction main peaks at about 13.8, 14.4, 17.4, 17.8, 21.8, 22.2, 25.8, 27.8±0.2 degrees two theta.

Figure 21:
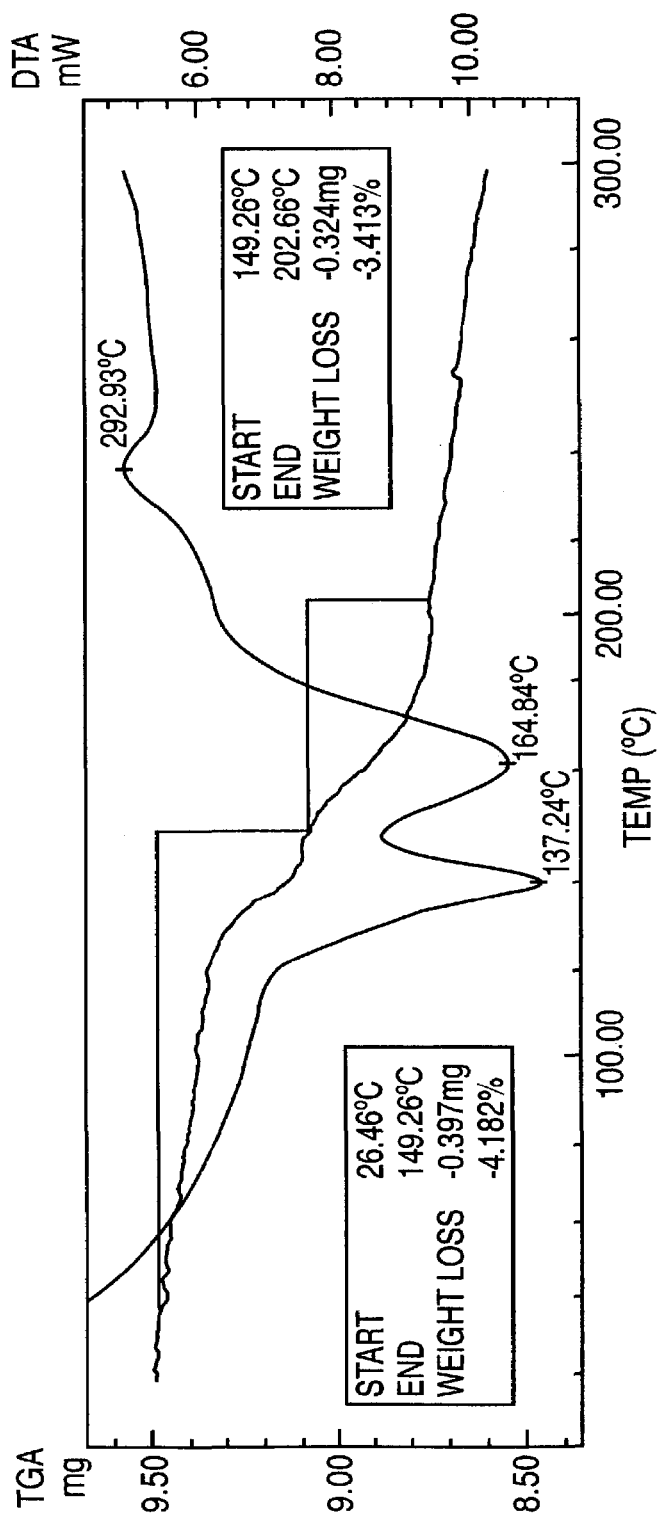
FIG. 21 depicts the Differential Thermal Gravimetry (DTG) of BOS—Ca novel Form I.

X-Ray Powder Diffraction pattern is given in FIG. 21.

DTG

DTG profile of BOS—H monohydrate novel form I is characterized by two endothermic peak at about 120 and 175° C. A weight loss step of about 9% is observed in this temperature range.

Figure 22:
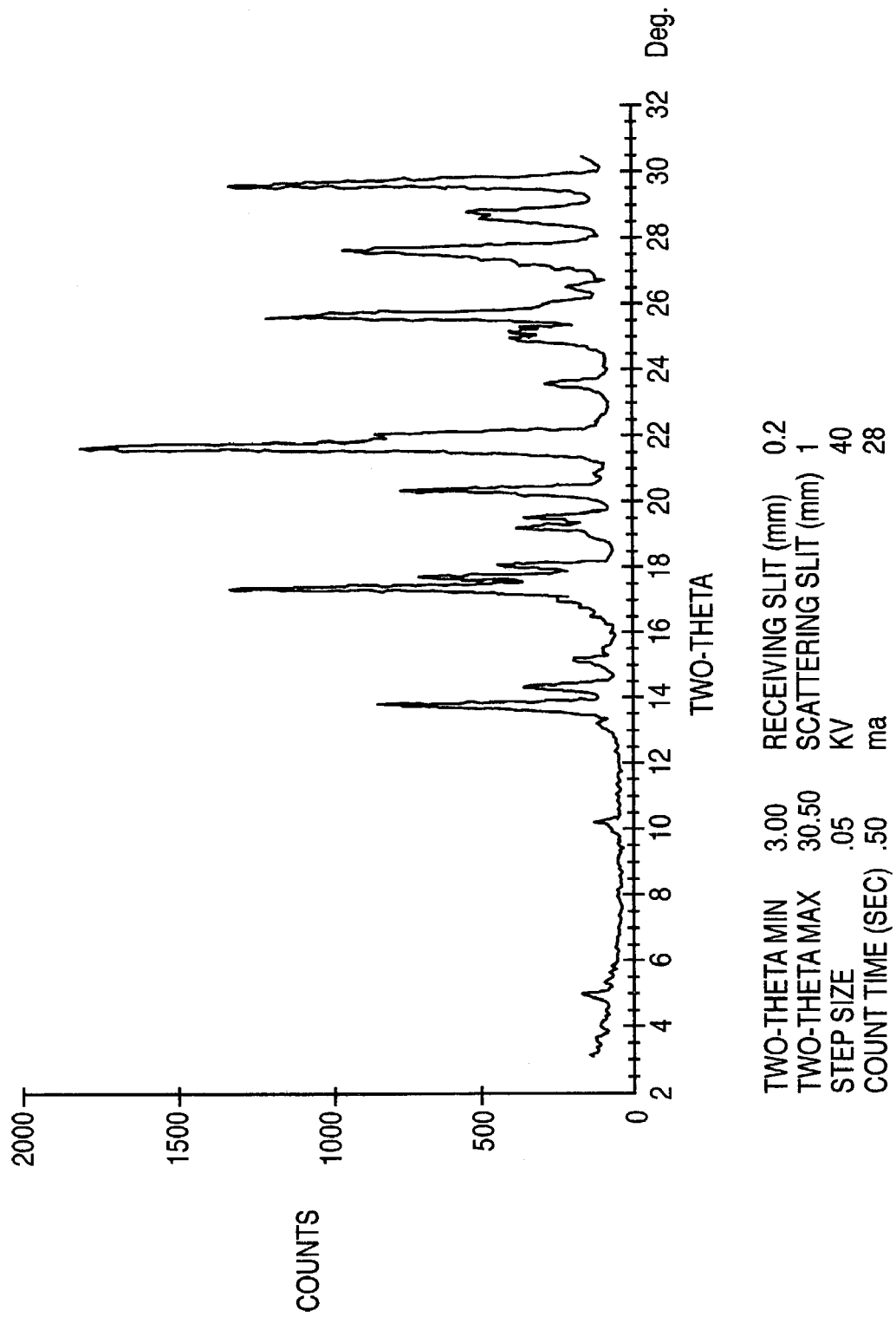
FIG. 22 depicts the X-ray Powder Diffraction (XRD) Pattern for BOS—H monohydrate novel Form I.
Figure 23:
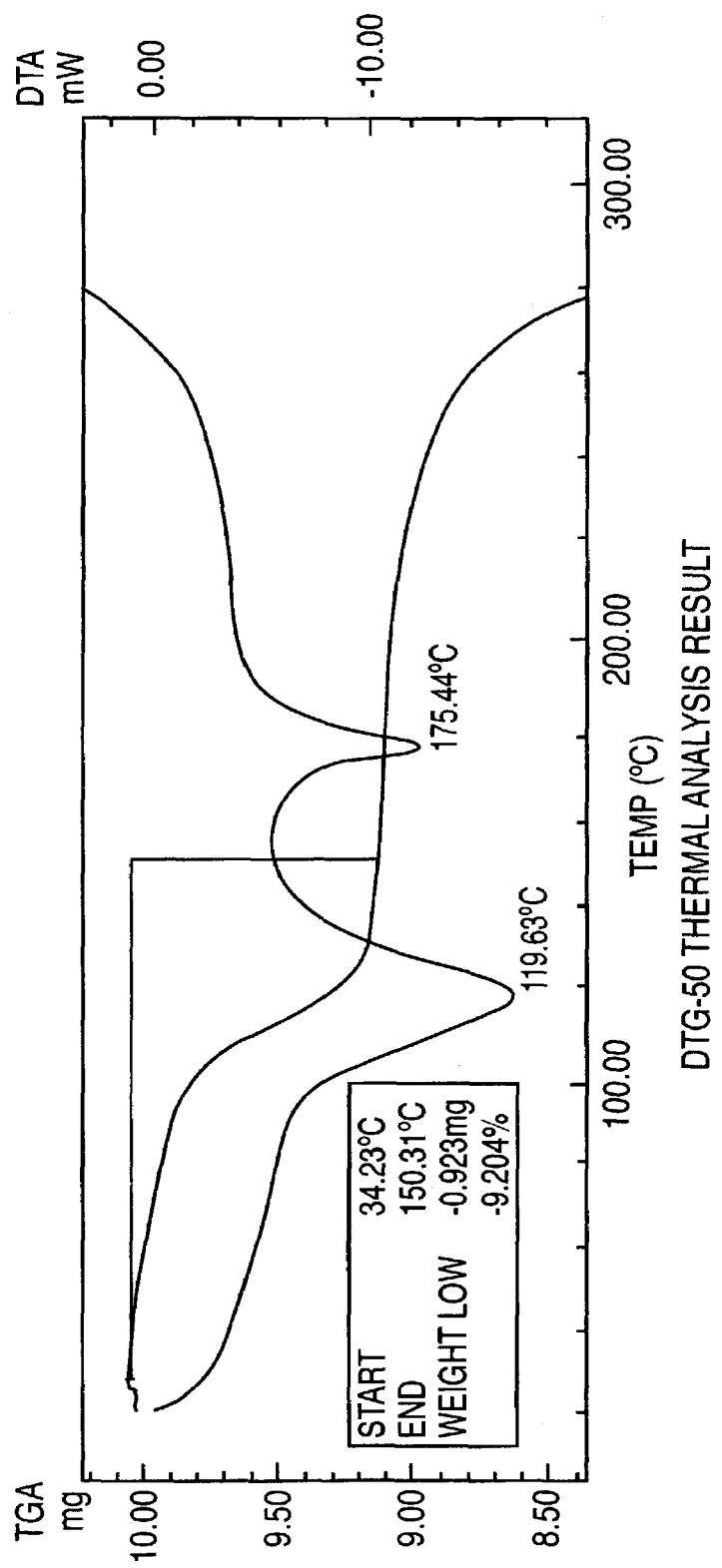
FIG. 23 depicts the Differential Thermal Gravimetry (DTG) of BOS—H monohydrate novel Form I.

DTG thermogram of BOS—H monohydrate novel form I is given in FIG. 22.

KF

Water content of BOS—H novel form I as was measured by KF titration is about 7.6%. This value is coincident with the expected water content for monohydrate form.

The invention will be better understood from the following experimental details. These examples are provided to illustrate specific embodiments of the present invention but they are not intended to be limiting in any way.

Experimental Procedure: Preparation of Crystalline Forms of BOS

Preparation of BOS—H Monohydrate

The solution of chlorosulfonic acid (13 ml, 25.5 mmol) in methylene chloride (100 ml) was cooled to ~–10° C. Dioxane (22.5 grams, 25.5 mmol) was added at this temperature followed by the addition of BOA (30 grams, 16.9 mmol). The obtained slurry was than heated at reflux for 2.5 hours. The reaction mixture was stirred at room temperature over night and after this was held with ice.

The aqueous phase was extracted with methylene chloride and then evaporated to dryness on rotavapor. The solid was dried for two days at 60° C. and for ~16 hours at 100° C. The product is BOS—H monohydrate (KF 2.8%).

Preparation of BOS—Na Monohydrate Form I

To the chilled solution (0° C.) of chlorosulfonic acid (136 grams, 1.167 mol) in ethyl acetate (400 ml) was added drop-wise dioxane (103 grams, 1.169 mol) followed by the addition of BOA (180 grams, 1.017 mol). The mixture was than heated at about 55° C. for about 16 hours. After the reaction completion, the mixture has been cooled to room temperature and ice-water was added. The aqueous phase was treated with aqueous NaOH until pH 10.

The product was isolated by evaporation to dryness of the aqueous solution and n-BuOH. The obtained solid was than dried in oven at 80° C. BOS—Na (271 grams) was obtained; the solid does not contain water (KF 0.002%). BOS—Na dry was kept in a closed bottle at room temperature. After about 5 months the KF analysis (7.3%) indicates the formation of hydrate-BOS—Na monohydrate Form I.

Preparation of BOS—Na Monohydrate Form I

To the solution of BOA (5 grams, 28.25 mmol) in ethyl acetate (30 ml), acetic anhydride (3.75 grams, 36.73 mmol) and sulfuric acid 98% (3.6 grams, 36.73 mmol) were added. During the addition of sulfuric acid the temperature reached ~30° C. Then the reaction mixture was heated at reflux for 1.5 hour.

More sulfonating reagent was added (2.1 grams acetic anhydride and 2 grams sulfuric acid) and the reflux was continued for over one hour. The reaction mixture was then cooled to room temperature and held with aqueous 10% NaOH (32 ml). The product precipitates upon cooling to ~5° C. The solid was washed with ethyl acetate and dried at 80° C. for 2 days. The obtained BOS—Na (6.3 grams) contains 1.7% water (by KF). This solid was exposed to the laboratory humidity for one week; the obtained solid is BOS—Na monohydrate Form I.

Preparation of BOS—Na Form II

The solution of acetic anhydride (3.75 grams, 36.73 mmol) and sulfuric acid 98% (3.6 grams, 36.73 mmol) in ethyl acetate (30 ml) has been cooled to –5° C. BOA (5 grams, 28.25 mmol) was added and the reaction mixture had been heated at reflux for ~3 hours.

After cooling to room temperature the reaction mixture was held with aqueous 10% NaOH and cooled to ~5° C. to precipitate the product; the solid was dried for 2 days in oven at 80° C. BOS—Na (4.9 grams) (KF 1.83%) is BOS—Na Form II.

Preparation of BOS—Na Form III

The solution of acetic anhydride (5.75 grams, 56.32 mmol) and sulfuric acid 98% (5.5 grams, 56.12 mmol) in toluene (30 ml) was cooled to ~0° C. BOA was added (5 grams, 28.25 grams) and the reaction mixture was heated at reflux for 5 hours. More sulfonating reagent was added (3 grams acetic anhydride and 2.9 grams sulfuric acid) and the reflux was maintained for one additional hour.

The reaction mixture was cooled to room temperature and treated with NaOH pearls to precipitate the product upon cooling. The solid was washed with toluene, filtrated and dried at 80° C. for two days. The product is BOS—Na Form III.

Preparation of BOS—Na Form IV

To a three necked flask equipped with thermometer, mechanical stirrer and condenser, BOS—Na (50 grams) and absolute ethanol (750 mL). The obtained slurry was then heated at reflux. A gel-like material was obtained. An additional 150 mL of ethanol was added. The solvent was removed-on rotavapor. The solid material obtained after the ethanol evaoporation weighted 33.23 grams. The product is BOS—Na Form IV (KF 2.7%).

The process for preparing BOS—Na Form IV were performed using other lower alkly alochols including isopropanol, methanol and ethanol (75%–99.9%).

Preparation of BOS—Na Form V

To the chilled (0° C.) solution of acetic anhydride (1.3 eq.) and BOA in ethyl acetate, $H_2SO_4$ (1.3 eq.) was added drop-wise.

The reaction mixture was heated at reflux and then stirred at reflux until the reaction completion (~5 hours). After this, the mixture was cooled to ~25° C. and treated with NaOH. The reaction product precipitatd on cooling to ~5° C. The solid was filtrated and washed with ethyl acetate.

The crystalline form was obtained during the production of BOS—Na in industrial scale. The preparation of BOS—Na is the laboratory procedure adapted to the large scale. The wet material obtained according to this procedure in the industrial batch was dried in an industrial drier:

| | |
|---|---|
| Vacuum: | 30 mmHg |
| Temperature in the jacket: | 85° C. |
| Mechanical stirring | Several days until the water |
| Time: | content was less than 1.5%. |

Preparation of BOS—Ba Monohydrate

To the chilled solution of chlorosulfonic acid (13 ml, 19.5 mmol) in methylene chloride. 10 ml dioxane (17.25 grams, 16.9 mmol) and BOA (30 grams, 16.9 mmol) were added. The reaction mixture was heated at reflux for 4.5 hours.

After this the reaction mixture was cooled to room temperature and ice was added. The aqueous phase was extracted with methylene chloride and then held with $Ba(OH)_2$ (56 grams); the solid was filtrated, washed with water and dried in oven at 100° C. for 5 hours. The product is BOS—Ba monohydrate.

Preparation of BOS—Ca Dihydrate

To the chilled at (−5° C.) solution of chlorosulfonic acid (13 ml, 19.5 mmol) in methylene chloride (100 ml) dioxane (17.2 grams, 19.5 mmol) and BOA (30 grams, 16.9 mmol) were added. Then the reaction mixture was heated at reflux for 5 hours.

After the reaction completion, ice was added to the cooled reaction mixture and the aqueous phase was treated with $Ca(OH)_2$ until pH 12. The product precipitate after stirring for ~16 hours. The solid was filtrated, washed with water and then with hexane and dried in oven at 60° C. The product is BOS—Ca dihydrate.

From the above it is clear that the invention provides crystalline forms of benzisoxazole methane sulfonic acid (BOS—H) and its salts (BOS—Na, BOS—Ca, BOS—Ba). The present invention further provides the BOS in its acid form and BOS as salts, both represent intermediates in the preparation of zonisamide.

It is contemplated that various modifications of the described modes of carrying out the invention will be apparent to those skilled in the art without departing from the scope and spirit of the invention.

What is claimed is:

1. A crystalline sodium salt of benzisoxazole methane sulfonic acid Form IV, characterized by an X-Ray Powder Diffraction (XRD) pattern having main peaks at about 4.5, 5.9, 8.8, 11.3, 16.3, 16.9, 19.0, 22.5, 23.9, 24.7, 25.0, 26.8, 28.1, 29.7, 30.9, 32.6, 33.6 35.5, and 36.6±0.2 degrees two theta.

2. A crystalline sodium salt of benzisoxazole methane sulfonic acid Form IV according to claim 1, further characterized by a Fourier Transform Infra Red Spectroscopy (FTIR) spectrum having peaks at about 3431, 1567, 1416, 924, 862 and 586 $cm^{-1}$.

3. The crystalline sodium salt of benzisoxazole methane sulfonic acid Form IV of claim 1, wherein the crystalline sodium salt of benzisoxazole methane sulfonic acid Form IV has a water content of about 2.9%.

4. The crystalline sodium salt of benzisoxazole methane sulfonic acid Form IV of claim 1, characterized by a differential thermogravimetric profile having an endothermic peak at about 50° C. and a weight loss step of about 2.9%.

5. The crystalline sodium salt of benzisoxazole methane sulfonic acid Form IV of claim 2, further characterized by a differential thermogravimetric profile having an endothermic peak at about 50° C. and a weight loss step of about 2.9%.

6. The crystalline sodium salt of benzisoxazole methane sulfonic acid Form IV of claim 2, having a water content of about 2.9%.

\* \* \* \* \*